(12) United States Patent
Zu

(10) Patent No.: US 10,683,506 B2
(45) Date of Patent: Jun. 16, 2020

(54) CD117 LIGAND-DRUG CONJUGATES FOR TARGETED CANCER THERAPY

(71) Applicant: THE METHODIST HOSPITAL SYSTEM, Houston, TX (US)

(72) Inventor: Youli Zu, Bellaire, TX (US)

(*) Notice: Subject to any disclaimer, the term of this patent is extended or adjusted under 35 U.S.C. 154(b) by 0 days.

(21) Appl. No.: 15/565,667

(22) PCT Filed: Apr. 8, 2016

(86) PCT No.: PCT/US2016/026675
§ 371 (c)(1),
(2) Date: Oct. 10, 2017

(87) PCT Pub. No.: WO2016/164745
PCT Pub. Date: Oct. 13, 2016

(65) Prior Publication Data
US 2018/0073027 A1 Mar. 15, 2018

Related U.S. Application Data

(60) Provisional application No. 62/145,774, filed on Apr. 10, 2015.

(51) Int. Cl.
*C12N 15/11* (2006.01)
*C12N 15/115* (2010.01)
*C07K 14/475* (2006.01)
*G01N 33/574* (2006.01)

(52) U.S. Cl.
CPC .......... *C12N 15/115* (2013.01); *C07K 14/475* (2013.01); *G01N 33/57407* (2013.01); *C12N 2310/16* (2013.01); *C12N 2310/351* (2013.01); *G01N 2800/50* (2013.01)

(58) Field of Classification Search
None
See application file for complete search history.

*Primary Examiner* — Ekaterina Poliakova-Georgantas
(74) *Attorney, Agent, or Firm* — Michael D. Eisenberg

(57) ABSTRACT

Disclosed are compositions and methods relating to nucleic acid aptamers that specifically target CD117 protein and also selective binding to CD117-expressing cells. The ligand-drug conjugates specifically target CD117-expressing cells and subsequently internalize into the cells, leading apoptosis, growth inhibition, and death of cells of interest and no off-target toxicity to CD117-negative normal cells.

19 Claims, 7 Drawing Sheets

Specification includes a Sequence Listing.

```
                            SEQUENCE LISTING

<160> NUMBER OF SEQ ID NOS: 11

<210> SEQ ID NO 1
<211> LENGTH: 35
<212> TYPE: DNA
<213> ORGANISM: ARTIFICIAL SEQUENCE
<220> FEATURE:
<223> OTHER INFORMATION: SYNTHETIC

<400> SEQUENCE: 1
attgcacggg gatcgagcag gggaccaggt gaatg                                 35

<210> SEQ ID NO 2
<211> LENGTH: 21
<212> TYPE: DNA
<213> ORGANISM: ARTIFICIAL SEQUENCE
<220> FEATURE:
<223> OTHER INFORMATION: SYNTHETIC

<400> SEQUENCE: 2
gaggcatacc agcttattca a                                               21

<210> SEQ ID NO 3
<211> LENGTH: 21
<212> TYPE: DNA
<213> ORGANISM: ARTIFICIAL SEQUENCE
<220> FEATURE:
<223> OTHER INFORMATION: SYNTHETIC

<400> SEQUENCE: 3
ttcgcagatt gcacttacta t                                               21

<210> SEQ ID NO 4
<211> LENGTH: 35
<212> TYPE: DNA
<213> ORGANISM: Artificial Sequence
<220> FEATURE:
<223> OTHER INFORMATION: SYNTHETIC

<400> SEQUENCE: 4
ggggccgggg caagggggggg gtaccgtggt aggac                               35

<210> SEQ ID NO 5
<211> LENGTH: 35
<212> TYPE: DNA
<213> ORGANISM: ARTIFICIAL SEQUENCE
<220> FEATURE:
<223> OTHER INFORMATION: SYNTHETIC

<400> SEQUENCE: 5
ggggccgggg caagggggggg gtaacgtggt aggac                               35

<210> SEQ ID NO 6
<211> LENGTH: 35
<212> TYPE: DNA
<213> ORGANISM: ARTIFICIAL SEQUENCE
<220> FEATURE:
<223> OTHER INFORMATION: SYNTHETIC

<400> SEQUENCE: 6
ggggccgggg caagggggggg gtacggtggt aggac                               35
```

```
<210> SEQ ID NO 7
<211> LENGTH: 34
<212> TYPE: DNA
<213> ORGANISM: ARTIFICIAL SEQUENCE
<220> FEATURE:
<223> OTHER INFORMATION: SYNTHETIC

<400> SEQUENCE: 7
ggggccgggg caagggggggg taccgtggta ggac                              34

<210> SEQ ID NO 8
<211> LENGTH: 77
<212> TYPE: DNA
<213> ORGANISM: ARTIFICIAL SEQUENCE
<220> FEATURE:
<223> OTHER INFORMATION: SYNTHETIC

<400> SEQUENCE: 8
gaggcatacc agcttattca aattgcacgg ggatcgagca ggggaccagg tgaatgatag   60
taagtgcaat ctgcgaa                                                 77

<210> SEQ ID NO 9
<211> LENGTH: 77
<212> TYPE: DNA
<213> ORGANISM: ARTIFICIAL SEQUENCE
<220> FEATURE:
<223> OTHER INFORMATION: SYNTHETIC

<400> SEQUENCE: 9
gaggcatacc agcttattca aggggccggg gcaagggggg ggtaccgtgg taggacatag   60
taagtgcaat ctgcgaa                                                 77

<210> SEQ ID NO 10
<211> LENGTH: 56
<212> TYPE: DNA
<213> ORGANISM: ARTIFICIAL SEQUENCE
<220> FEATURE:
<223> OTHER INFORMATION: SYNTHETIC

<400> SEQUENCE: 10
ggggccgggg caagggggggg gtaccgtggt aggacatagt aagtgcaatc tgcgaa     56

<210> SEQ ID NO 11
<211> LENGTH: 56
<212> TYPE: DNA
<213> ORGANISM: ARTIFICIAL SEQUENCE
<220> FEATURE:
<223> OTHER INFORMATION: SYNTHETIC

<400> SEQUENCE: 11
gaggcatacc agcttattca aggggccggg gcaagggggg ggtaccgtgg taggac      56
```

CD117 LIGAND-DRUG CONJUGATES FOR TARGETED CANCER THERAPY

CROSS-REFERENCE TO RELATED APPLICATIONS

This application claims benefit of U.S. Provisional Application No. 62/145,774, filed Apr. 10, 2015, which is hereby incorporated herein by reference in its entirety.

ACKNOWLEDGEMENT OF GOVERNMENT SUPPORT

This invention was made with government support under Grants No. R01CA151955 and R33CA173382 awarded by the National Institutes of Health. The government has certain rights in this invention.

BACKGROUND

The current treatment paradigm for acute myeloid leukemia (AML) is remission induction chemotherapy, followed by either consolidation chemotherapy or allogeneic stem cell transplantation (Mayer R J, Davis R B, Schiffer C A, Berg D T, Powell B L, Schulman P, Omura G A, Moore J O, McIntyre O R, Frei E, 3rd: Intensive postremission chemotherapy in adults with acute myeloid leukemia. Cancer and Leukemia Group B. The New England journal of medicine 1994, 331(14):896-903; Burnett A K: Treatment of acute myeloid leukemia: are we making progress? Hematology/the Education Program of the American Society of Hematology American Society of Hematology Education Program 2012, 2012:1-6; Klimek V M: Recent advances in the management of therapy-related myelodysplastic syndromes and acute myeloid leukemia. Current opinion in hematology 2013, 20(2):137-143; Stone R M: Consolidation chemotherapy for adults with AML in first remission: is there a best choice? Journal of clinical oncology: official journal of the American Society of Clinical Oncology 2013, 31(17):2067-2069.). As most patients diagnosed with AML are in their sixth or seventh decade of life, many are not candidates for standard remission induction chemotherapy because of the adverse toxicities, such as profound myelosuppression, life-threatening infections, and cardiotoxicity (Martner A, Thoren F B, Aurelius J, Hellstrand K: Immunotherapeutic strategies for relapse control in acute myeloid leukemia. Blood reviews 2013, 27(5):209-216; Peloquin G L, Chen Y B, Fathi A T: The evolving landscape in the therapy of acute myeloid leukemia. Protein & cell 2013, 4(10):735-746; Nazha A, Ravandi F: Acute myeloid leukemia in the elderly: do we know who should be treated and how? Leukemia & lymphoma 2014, 55(5):979-987; Ferrara F: Conventional chemotherapy or hypomethylating agents for older patients with acute myeloid leukemia? Hematological oncology 2014, 32(1):1-9). The development of new effective and safe treatments for AML is therefore needed. The "ideal" therapy should specifically target AML tumor cells with no side-effect on normal cells (Snauwaert S, Vandekerckhove B, Kerre T: Can immunotherapy specifically target acute myeloid leukemic stem cells? Oncoimmunology 2013, 2(2): e22943; Sweet K, Lancet J E: Novel therapeutics in acute myeloid leukemia. Current hematologic malignancy reports 2014, 9(2):109-117; Li K, Lv X X, Hua F, Lin H, Sun W, Cao W B, Fu X M, Xie J, Yu J J, Li Z et al: Targeting acute myeloid leukemia with a proapoptotic peptide conjugated to a Toll-like receptor 2-mediated cell-penetrating peptide. International journal of cancer Journal international du cancer 2014, 134(3):692-702; Konig H, Levis M: Is targeted therapy feasible in acute myelogenous leukemia? Current hematologic malignancy reports 2014, 9(2):118-127; Walter R B: The role of CD33 as therapeutic target in acute myeloid leukemia. Expert opinion on therapeutic targets 2014, 18(7): 715-718). Since CD117 (c-Kit) is a transmembrane receptor on tumor cells surface and expresses on myeloid leukemia cells in 64% of patients with de novo AML and 95% of those with relapsed AML (Hans C P, Finn W G, Singleton T P, Schnitzer B, Ross C W: Usefulness of anti-CD117 in the flow cytometric analysis of acute leukemia. American journal of clinical pathology 2002, 117(2):301-305). Furthermore, CD117-expressing AML patients survived significantly shorter than CD117-negative patients and CD117 receptor high expressed at low complete remission rate (Doepfner K T, Boller D, Arcaro A: Targeting receptor tyrosine kinase signaling in acute myeloid leukemia. Critical reviews in oncology/hematology 2007, 63(3):215-230; Stirewalt D L, Meshinchi S: Receptor tyrosine kinase alterations in AML—biology and therapy. Cancer treatment and research 2010, 145:85-108; Marcucci G, Haferlach T, Dohner H: Molecular genetics of adult acute myeloid leukemia: prognostic and therapeutic implications. Journal of Clinical Oncology: 2011, 29(5):475-486; Ashman L K, Griffith R: Therapeutic targeting of c-KIT in cancer. Expert opinion on investigational drugs 2013, 22(1):103-115; Liang J, Wu Y L, Chen B J, Zhang W, Tanaka Y, Sugiyama H: The C-kit receptor-mediated signal transduction and tumor-related diseases. International journal of biological sciences 2013, 9(5):435-443, indicating that CD117 receptor represents a potential therapeutic target for AML).

Aptamers are synthetic single-stranded oligonucleotides (DNA or RNA), which have the ability to specifically bind to their targets with high affinity (Banerjee J, Nilsen-Hamilton M: Aptamers: multifunctional molecules for biomedical research. Journal of molecular medicine 2013, 91(12): 1333-1342). As a "chemical antibody", aptamers can be chemically synthesized, easily conjugated with therapeutic drugs, and more importantly, less or not immunogenic (Kanwar J R, Shankaranarayanan J S, Gurudevan S, Kanwar R K: Aptamer-based therapeutics of the past, present and future: from the perspective of eye-related diseases. Drug discovery today 2014; Xing H, Hwang K, Li J, Torabi S F, Lu Y: DNA Aptamer Technology for Personalized Medicine. Current opinion in chemical engineering 2014, 4:79-87; Zhou J, Rossi J J: Cell-type-specific, Aptamer-functionalized Agents for Targeted Disease Therapy. Molecular therapy Nucleic acids 2014, 3:e169; Hong B, Zu Y: Detecting circulating tumor cells: current challenges and new trends. Theranostics 2013, 3(6):377-394; Li X, Zhao Q, Qiu L: Smart ligand: aptamer-mediated targeted delivery of chemotherapeutic drugs and siRNA for cancer therapy. Journal of controlled release: official journal of the Controlled Release Society 2013, 171(2):152-162). Similarly to protein antibodies, synthetic aptamers have been widely studied as specific ligands to target cell surface biomarkers (Li X, Zhao Q, Qiu L: Smart ligand: aptamer-mediated targeted delivery of chemotherapeutic drugs and siRNA for cancer therapy. Journal of controlled release: official journal of the Controlled Release Society 2013, 171(2):152-162; Barbas A S, Mi J, Clary B M, White R R: Aptamer applications for targeted cancer therapy. Future oncology 2010, 6(7):1117-1126; Lassalle H P, Marchal S, Guillemin F, Reinhard A, Bezdetnaya L: Aptamers as remarkable diagnostic and therapeutic agents in cancer treatment. Current drug metabolism 2012, 13(8):1130-1144; Pednekar P P, Jadhav K R, Kadam V J: Aptamer-dendrimer bioconjugate:

a nanotool for therapeutics, diagnosis, and imaging. Expert opinion on drug delivery 2012, 9(10):1273-1288; Radom F, Jurek P M, Mazurek M P, Otlewski J, Jelen F: Aptamers: molecules of great potential. Biotechnology advances 2013, 31(8):1260-1274; Zhao N, Pei S N, Parekh P, Salazar E, Zu Y: Blocking interaction of viral gp120 and CD4-expressing T cells by single-stranded DNA aptamers. The international journal of biochemistry & cell biology 2014, 51:10-18) for tumor cell detection and targeted therapy (Zhao N, You J, Zeng Z, Li C, Zu Y: An ultra pH-sensitive and aptamer-equipped nanoscale drug-delivery system for selective killing of tumor cells. Small 2013, 9(20):3477-3484). Recent studies reveal that antibody-drug conjugates are of a new biotherapeutics for targeted cancer therapy (Junutula J R, Raab H, Clark S, Bhakta S, Leipold D D, Weir S, Chen Y, Simpson M, Tsai S P, Dennis M S et al: Site-specific conjugation of a cytotoxic drug to an antibody improves the therapeutic index. Nature biotechnology 2008, 26(8):925-932; Adem Y T, Schwarz K A, Duenas E, Patapoff T W, Galush W J, Esue O: Auristatin antibody drug conjugate physical instability and the role of drug payload. Bioconjugate chemistry 2014, 25(4):656-664; Fauvel B, Yasri A: Antibodies directed against receptor tyrosine kinases: Current and future strategies to fight cancer. mAbs 2014, 6(4):838-851; Sievers E L, Senter P D: Antibody-drug conjugates in cancer therapy. Annual review of medicine 2013, 64:15-29). Notably, in comparing to protein antibodies the synthetic aptamers are smaller in size, and thus exhibits higher tissue penetration efficiency and faster binding capacity to tumor cells (Zeng Z, Zhang P, Zhao N, Sheehan A M, Tung C H, Chang C C, Zu Y: Using oligonucleotide aptamer probes for immunostaining of formalin-fixed and paraffin-embedded tissues. Modern pathology: an official journal of the United States and Canadian Academy of Pathology, Inc 2010, 23(12):1553-1558; Shigdar S, Lin J, Yu Y, Pastuovic M, Wei M, Duan W: RNA aptamer against a cancer stem cell marker epithelial cell adhesion molecule. Cancer science 2011, 102(5):991-998). These advanced chemical and biological features indicate potential value of synthetic aptamers in biomedical studies and clinical applications.

What is needed in the art is ssDNA ligands that specifically target CD117 proteins and selectively bind to CD117-expressing cells.

SUMMARY

Disclosed herein is an aptamer-agent conjugate comprising: a nucleic acid aptamer comprising a region that interacts with a CD1 17-expressing cell, and an agent, wherein the nucleic acid aptamer comprises SEQ ID NO: 1 or SEQ ID NO: or SEQ ID NO: 5 or SEQ ID NO: 6.

Also disclosed is an isolated nucleic acid molecule comprising SEQ ID NO: 1 or SEQ ID NO: 4 or SEQ ID NO: 5 or SEQ ID NO: 6.

Further disclosed is a pharmaceutical composition comprising the conjugates disclosed herein, wherein the agent is a therapeutic agent.

Also disclosed is a method of targeting CD117 cells with an agent, the method comprising conjugating a nucleic acid aptamer comprising a region that interacts with a CD117 cell to the agent, and exposing CD117 cells to the aptamer/agent conjugate, wherein the nucleic acid comprises SEQ ID NO: 1 or SEQ ID NO: 4 or SEQ ID NO: 5 or SEQ ID NO: 6.

Disclosed herein is a method of treating a subject with cancer, the method comprising: identifying a subject in need of treatment for cancer, and administering a pharmaceutical composition to the subject, wherein the pharmaceutical composition comprises a conjugate of a nucleic acid aptamer and a cancer treating agent, wherein the nucleic acid aptamer comprises a region that interacts with a CD117 cell, thereby treating cancer in the subject, wherein the nucleic acid aptamer comprises SEQ ID NO: 1 or SEQ ID NO: 4 or SEQ ID NO: 5 or SEQ ID NO: 6.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
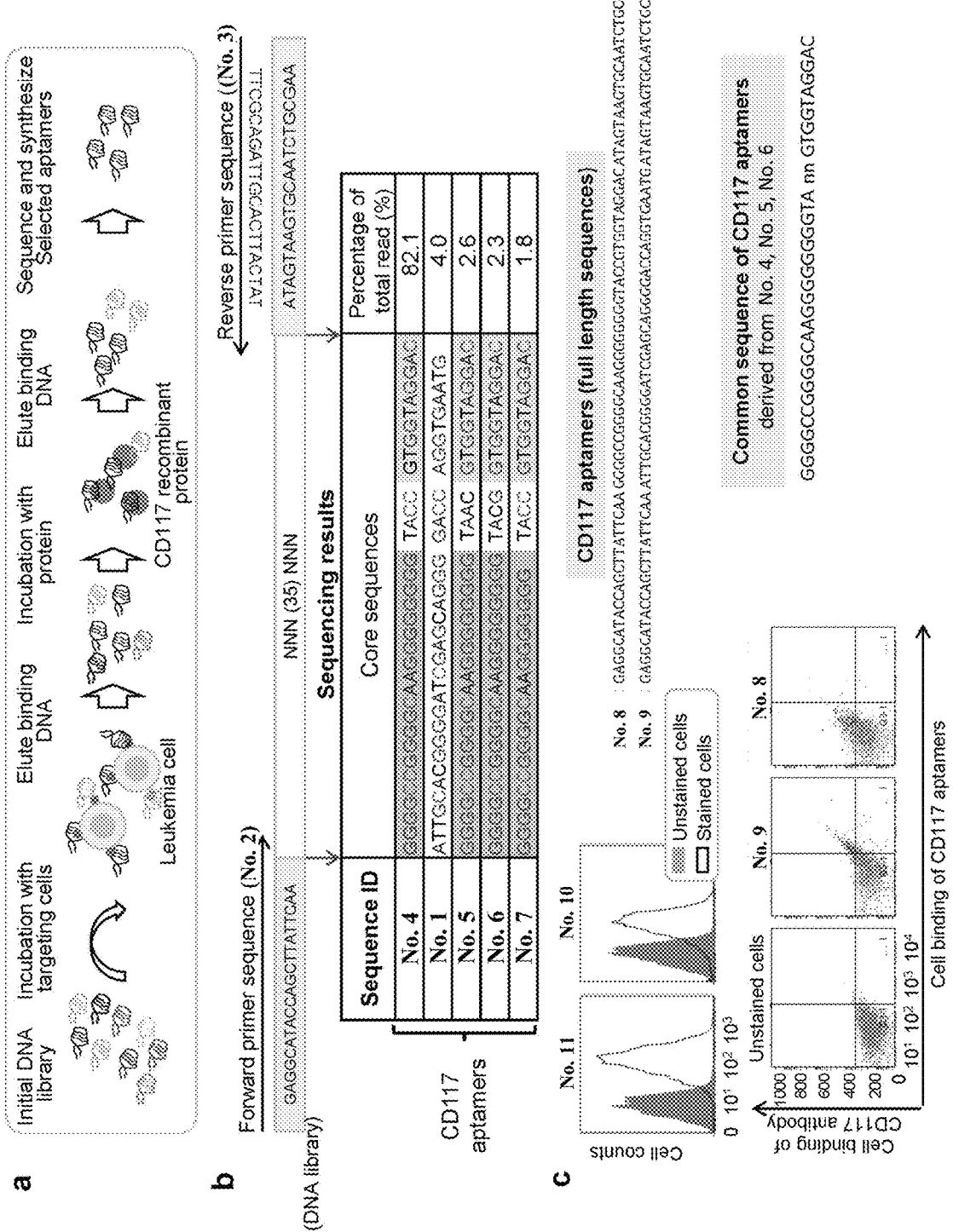
FIG. 1 shows an aptamer selection process and the identification of the developed aptamers: (a) The process of the aptamer selection by cell-based enrichment and protein-based selection. (b) Sequences of DNA library (77nt), including forward primer sequence (21nt) (SEQ ID NO: 2), 35nt random sequence and reverse primer sequence (21nt) (SEQ ID NO: 3). The first five dominant sequences and the percentage of the individual sequence in total reads (SEQ ID NOS: 1, 4, 5, 6, and 7, respectively). (c) Binding ability of aptamer No. 9 and No. 8 to CD117 positive cells HEL and AML specimen by flow cytometry detection. Analysis of CD117 aptamers No. 6, No. 7, and No. 8 resulted in a common sequence.

The materials, compounds, compositions, articles, and methods described herein may be understood more readily by reference to the following detailed description of specific aspects of the disclosed subject matter and the Examples included therein and to the Figures.

Before the present materials, compounds, compositions, articles, and methods are disclosed and described, it is to be understood that the aspects described below are not limited to specific synthetic methods or specific reagents, as such may, of course, vary. It is also to be understood that the terminology used herein is for the purpose of describing particular aspects only and, unless a particular term is specifically defined herein, is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Definitions

As used herein, the term "nucleic acid" and "polynucleotide" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides.

Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

The term "nucleotide sequence" refers to a polymer of DNA or RNA which can be single- or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" may also be used interchangeably with gene, cDNA, DNA and RNA encoded by a gene, e.g., genomic DNA, and even synthetic DNA sequences. The term also includes sequences that include any of the known base analogs of DNA and RNA.

By "fragment" or "portion" is meant a full length or less than full length of the nucleotide sequence.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have in at least one embodiment 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

The term "gene" is used broadly to refer to any segment of nucleic acid associated with a biological function. Genes include coding sequences and/or the regulatory sequences required for their expression. For example, gene refers to a nucleic acid fragment that expresses mRNA, functional RNA, or a specific protein, including its regulatory sequences. Genes also include non-expressed DNA segments that, for example, form recognition sequences for other proteins.

Genes can be obtained from a variety of sources, including cloning from a source of interest or synthesizing from known or predicted sequence information, and may include sequences designed to have desired parameters. In addition, a "gene" or a "recombinant gene" refers to a nucleic acid molecule comprising an open reading frame and including at least one exon and (optionally) an intron sequence. The term "intron" refers to a DNA sequence present in a given gene which is not translated into protein and is generally found between exons.

"Naturally occurring," "native" or "wild type" is used to describe an object that can be found in nature as distinct from being artificially produced. For example, a nucleotide sequence present in an organism (including a virus), which can be isolated from a source in nature and which has not been intentionally modified in the laboratory, is naturally occurring. Furthermore, "wild-type" refers to the normal gene, or organism found in nature without any known mutation.

"Operably-linked" nucleic acids refers to the association of nucleic acid sequences on single nucleic acid fragment so that the function of one is affected by the other, e.g., an arrangement of elements wherein the components so described are configured so as to perform their usual function. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. Control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

The terms "isolated and/or purified" refer to in vitro isolation of a nucleic acid, e.g., a DNA or RNA molecule from its natural cellular environment, and from association with other components of the cell, such as nucleic acid or polypeptide, so that it can be sequenced, replicated, and/or expressed. For example, "isolated nucleic acid" may be a DNA molecule containing less than 31 sequential nucleotides that is transcribed into an RNAi molecule. Such an isolated RNAi molecule may, for example, form a hairpin structure with a duplex 21 base pairs in length that is complementary or hybridizes to a sequence in a gene of interest, and remains stably bound under stringent conditions (as defined by methods well known in the art, e.g., in Sambrook and Russell, 2001). Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

In addition to nucleic acid aptamers, the nucleic acid molecules of the invention can include other sequences which have a utility in the methods disclosed herein.

As used herein, the term "recombinant nucleic acid," e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome that has not been transformed with exogenous DNA. An example of preselected DNA "derived" from a source would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. Therefore, "recombinant DNA" includes completely synthetic DNA sequences, semi-synthetic DNA sequences, DNA sequences isolated from biological sources, and DNA sequences derived from RNA, as well as mixtures thereof.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

"Recombinant DNA molecule" is a combination of DNA sequences that are joined together using recombinant DNA technology and procedures used to join together DNA sequences as described, for example, in Sambrook and Russell (2001).

The terms "heterologous gene," "heterologous DNA sequence," "exogenous DNA sequence," "heterologous RNA sequence," "exogenous RNA sequence" or "heterologous nucleic acid" each refer to a sequence that either originates from a source foreign to the particular host cell, or is from the same source but is modified from its original or native form. Thus, a heterologous gene in a host cell includes a gene that is endogenous to the particular host cell but has been modified through, for example, the use of DNA shuffling. The terms also include non-naturally occurring multiple copies of a naturally occurring DNA or RNA sequence. Thus, the terms refer to a DNA or RNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA or RNA sequence is a sequence that is naturally associated with a host cell into which it is introduced.

"Genome" refers to the complete genetic material of an organism.

A "vector" is defined to include, inter alia, any viral vector, as well as any plasmid, cosmid, phage or binary vector in double or single stranded linear or circular form that may or may not be self-transmissible or mobilizable, and that can transform prokaryotic or eukaryotic host either by integration into the cellular genome or exist extrachromosomally (e.g., autonomous replicating plasmid with an origin of replication).

"Coding sequence" refers to a DNA or RNA sequence that codes for a specific amino acid sequence. It may constitute an "uninterrupted coding sequence", i.e., lacking an intron, such as in a cDNA, or it may include one or more introns bounded by appropriate splice junctions. An "intron" is a sequence of RNA that is contained in the primary transcript but is removed through cleavage and re-ligation of the RNA within the cell to create the mature mRNA that can be translated into a protein.

The terms "initiation codon" and "termination codon" refer to a unit of three adjacent nucleotides (a 'codon') in a coding sequence that specifies initiation and chain termination, respectively, of protein synthesis (mRNA translation).

"Functional RNA" refers to sense RNA, antisense RNA, ribozyme RNA, siRNA, or other RNA that may not be translated but yet has an effect on at least one cellular process.

The term "RNA transcript" or "transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" are nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, regulatable promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency.

"3' non-coding sequence" refers to nucleotide sequences located 3' (downstream) to a coding sequence and may include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, heterologous gene or nucleic acid segment, or a transgene in cells. For example, in the case of siRNA constructs, expression may refer to the transcription of the siRNA only. In addition, expression refers to the transcription and stable accumulation of sense (mRNA) or functional RNA. Expression may also refer to the production of protein.

"Altered levels" refers to the level of expression in transgenic cells or organisms that differs from that of normal or untransformed cells or organisms.

"Overexpression" refers to the level of expression in transgenic cells or organisms that exceeds levels of expression in normal or untransformed cells or organisms.

As used herein, the term "derived" or "directed to" with respect to a nucleotide molecule means that the molecule has complementary sequence identity to a particular molecule of interest.

"Treating" as used herein refers to ameliorating at least one symptom of, curing and/or preventing the development of a disease or a condition.

The term "drug", as used herein, refers to a compound that is desirable to use in the body of an animal subject for a therapeutic and/or diagnostic purpose. Accordingly, the term "drug" encompasses, but is not limited to (i) conventional pharmaceutical compounds useful for the treatment of diseases or disorders, including, but not limited to, chemotherapeutic agents, antiinflammatory agents, ionotropic agents, antimicrobial agents, etc.; and hormones; (ii) peptide, protein, and peptidomimetic compounds including, but not limited to cytokines, immunoglobulin molecules and fragments thereof, single chain antibodies, and toxins; as well as (iii) imaging agents such as detectable labels including but not limited to radioactive labels; paramagnetic labels, etc.

An individual who is "suffering from" a disease, disorder, and/or condition has been diagnosed with or displays one or more symptoms of the disease, disorder, and/or condition.

An individual who is "susceptible to" a disease, disorder, and/or condition has not been diagnosed with and/or may not exhibit symptoms of the disease, disorder, and/or condition. In some embodiments, an individual who is susceptible to a disease, disorder, and/or condition (e.g., cancer) may be characterized by one or more of the following: (1) a genetic mutation associated with development of the disease, disorder, and/or condition (e.g. a mutation in an oncogene-encoding gene); (2) a genetic polymorphism associated with development of the disease, disorder, and/or condition (e.g. a polymorphism in the promoter region of an oncogene-encoding gene); (3) increased and/or decreased expression and/or activity of a protein associated with the disease, disorder, and/or condition; (4) habits and/or lifestyles associated with development of the disease, disorder, and/or condition (e.g. smoking, obesity, unhealthy diet, lack of exercise); (5) a family history of the disease, disorder, and/or condition (e.g. parent with cancer); (6) infection by a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

As used herein, the term "target" or "marker" refers to any entity that is capable of specifically binding to a particular nucleic acid aptamer. In some embodiments, targets are specifically associated with one or more particular tissue types. In some embodiments, targets are specifically associated with one or more particular cell types. In some embodiments, targets are specifically associated with one or more particular disease states. In some embodiments, targets are specifically associated with one or more particular developmental stages. For example, a cell-specific aptamer can bind at least 3 fold, at least 4 fold, at least 5 fold, at least 6 fold, at least 7 fold, at least 8 fold, at least 9 fold, at least 10 fold, at least 50 fold, at least 100 fold, or at least 1000 fold greater than a control. In some embodiments, a target can comprise a protein, a carbohydrate, a lipid, and/or a nucleic acid, as described herein.

A substance is considered to be "targeted" for the purposes described herein if it specifically bound to a nucleic acid aptamer. In some embodiments, a nucleic acid aptamer specifically binds to a target under stringent conditions. A conjugate comprising a nucleic acid aptamer is considered to be "targeted" if the nucleic acid aptamer specifically binds to a target, thereby delivering the entire conjugate to a specific organ, tissue, cell, extracellular matrix component, and/or intracellular compartment.

As used herein, the phrase "therapeutic agent" refers to any agent that, when administered to a subject, has a therapeutic and/or diagnostic effect and/or elicits a desired biological and/or pharmacological effect.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels. For example, the conjugates disclosed herein can inhibit the growth or proliferation of cancer cells.

The terms "peptide," "protein," and "polypeptide" are used interchangeably to refer to a natural or synthetic molecule comprising two or more amino acids linked by the The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "specifically binds", as used herein, when referring to a peptide or receptor, refers to a binding reaction which is determinative of the presence of the protein or polypeptide or receptor in a heterogeneous population of proteins and other biologics. Thus, under designated conditions, a specified aptamer "specifically binds" to its particular "target" when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ M$^{-1}$ (e.g., $10^6$ M$^{-1}$, $10^7$ M$^{-1}$, $10^8$ M$^{-1}$, $10^9$ M$^{-1}$, $10^{10}$ M$^{-1}$, $10^{11}$ M$^{-1}$, and $10^{12}$ M$^{-1}$ or more) with that second molecule.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

Compositions and Methods

Targeted delivery can enhance therapeutic efficacy and also reduce off-target toxic effect of chemotherapeutic drugs. Since majority of Acute Myeloid Leukemia (AML) cells express high level of surface CD117, targeted therapy of AML by CD ligand can effectively enhance the therapeutic effect. Disclosed herein is a single strand DNA aptamer specific for CD117. The developed aptamer selectively bound to a CD117-expressing cell line, and was able to specifically immunoprecipitate endogenous CD117 protein from leukemia cell lysates. Moreover, it selectively targeted CD117-positive AML cells in patient marrow specimens with an identical staining pattern to that observed with anti-CD117 antibody, indicating its clinical value. For targeted therapy, Methotrexate (MTX), a vital component of AML chemotherapy regimens, was conjugated with the aptamer (Apt) to formulate Apt-MTX. The formed Apt-MTX conjugates specifically inhibited AML cell growth, induced G1 cell cycle arrest and cell apoptosis, but had little effect on the off-target CD117-negative cells in the same cultures. More importantly, validation study of AML patient/s marrow specimens demonstrated that Apt-MTX treatment were able to selectively inhibit primary AML cells and show minimal effect on background normal cells in the same specimens.

Disclosed herein is a targeted therapeutic approach for specific delivery and intracellular release of an agent payload (such as a drug) in cells, such as MM cells, thereby inhibiting tumor growth and improving survival. Notably, the conjugates disclosed herein can be used as a universal platform to treat different tumors by simply replacing the aptamer sequence that targets different biomarkers.

Aptamers

Disclosed herein is an aptamer-agent conjugate comprising: a nucleic acid aptamer comprising a region that interacts with a CD117 cell, and an agent.

Nucleic acid aptamers are characterized by a single-strand and have secondary structure that may possess one or more stems (i.e., base-paired regions) as well as one or more non base-paired regions along the length of the stem. These non-base-paired regions can be in the form of a bulge or loop (e.g., internal loop) along the length of the stem(s) and/or a loop at the end of the one or more stem(s) (e.g., hairpin loop). These nucleic acid aptamers possess specificity in binding to a particular target molecule, and they noncovalently bind their target molecule through an interaction such as an ion-ion force, dipole-dipole force, hydrogen bond, van der Waals force, electrostatic interaction, stacking interaction or any combination of these interactions.

As used herein, "nucleic acid" includes both DNA and RNA, in both D and L enantiomeric forms, as well as derivatives thereof (including, but not limited to, 2'-fluoro-, 2'-amino, 2'O-methyl, 5'iodo-, and 5'-bromo-modified polynucleotides). Nucleic acids containing modified nucleotides (Kubik et al., "Isolation and Characterization of 2'fluoro-, 2'amino-, and 2'fluoro-amino-modified RNA Ligands or Human IFN-gamma that Inhibit Receptor Binding," J. Immunol. 159:259-267 (1997); Pagratis et al., "Potent 2'-amino, and 2'-fluoro-2'-deoxy-ribonucleotide RNA Inhibitors of Keratinocyte Growth Factor," Nat. Biotechnol. 15:68-73 (1997), each which is hereby incorporated by reference in its entirety) and the L-nucleic acids, enantiomeric to natural D-nucleic acids (Klussmann et al., "Mirror-image RNA that Binds D-adenosine," Nat. Biotechnol. 14:1112-1115 (1996) and Williams et al., "Bioactive and nuclease-resistant L-DNA Ligand of Vasopressin," Proc. Natl. Acad. Sci. USA 94:11285-11290 (1997), each which is hereby incorporated by reference in its entirety), and non-natural bases are used to enhance biostability. In addition, the sugar-phosphate backbone can be replaced with a peptide backbone, forming a peptide nucleic acid (PNA), other natural or non-natural sugars can be used (e.g., 2'-deoxyribose sugars), or phosphothioate or phosphodithioate can be used instead of phosphodiester bonds. The use of locked nucleic acids (LNA) is also contemplated.

The aptamers disclosed herein can comprise various sequences. Specifically, the nucleic acid aptamer can comprise the sequence (5'-GGGGC-CGGGGCAAGGGGGGGGTAnnGTGGTAGGAC-3').
This is known as the "core sequence" of the aptamer, as it comprises the region which interacts with CD117. It is contemplated that the core sequence can comprise variants, such as deletions additions, and substitutions, and the sequence can vary at the "NN" region. Specifically, disclosed are variants of the sequence 5'-GGGGC-CGGGGCAAGGGGGGGGTAnnGTGGTAGGAC-3' with 65%, 70%, 75%, 80%, 85%, 90%, 95%, 96%, 97%, 98%, and 99% homology to the sequence 5'-GGGGC-CGGGGCAAGGGGGGGGTAnnGTGGTAGGAC-3', for example. For example, the core sequence vary by 1, 2, 3, 4, 5, 6, 7, 8, 9, or 10 nucleotides and still retain functionality. One of skill in the art will understand how to determine which nucleotides can be added, deleted, or substituted, while still allowing functionality of the aptamer, such as interaction with CD117. Sequence identity and homology is discussed in further detail herein.

In addition to the core sequence-5-GGGGC-CGGGGCAAGGGGGGGGTAnnGTGGTAGGAC-3', the aptamer can comprise the nucleic acid sequence found in SEQ ID NO: 1 (5'-ATTGCACGGGGATCGAGCA-GGGGACCAGGTGAATG-3'). Also disclosed are variants of SEQ ID NO: 1, with 65%, 70%, 75%, 80%, 85%, 90%, 95%, 96%, 97%, 98%, and 99% homology to SEQ ID NO: 1, for example.

Also disclosed herein are cell lines, vectors, and expression cassettes comprising the nucleic acid sequences disclosed herein, such as SEQ ID NO: 1 or SEQ ID NO: 4 or SEQ ID NO: 5 or SEQ ID NO: 6.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences.

Generally, the comparison window is at least 20 contiguous nucleotides in length, and optionally can be longer. For example, the core sequence 5'-GGGGC-CGGGGCAAGGGGGGGGTAnnGTGGTAGGAC-3' disclosed herein is 35 nucleotides in length, and can be used in the comparison window. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Software for performing BLAST analyses is publicly available through the National Center for Biotechnology Information (see the World Wide Web at ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When using BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix.

(c) As used herein, "sequence identity" or "identity" in the context of two nucleic acid sequences makes reference to a specified percentage of residues in the two sequences that are the same when aligned for maximum correspondence over a specified comparison window, as measured by sequence comparison algorithms or by visual inspection. When percentage of sequence identity is used in reference to proteins, it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%; at least 80%, 81%, 82%, 83%, 84%, 85%, 86%, 87%, 88%, or 89%; at least 90%, 91%, 92%, 93%, or 94%; or even at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions (see below). Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code.

(e)(ii) For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The Tm is the temperature (under defined ionic strength and pH) at which 50% of the target sequence hybridizes to a perfectly matched nucleic acid. Specificity is typically the function of post-hybridization washes, the critical factors being the ionic strength and temperature of the final wash solution. For DNA-DNA hybrids, the Tm can be approximated from the equation of Meinkoth and Wahl: Tm 81.5° C.+16.6 (log M)+0.41 (% GC)−0.61 (% form)−500/L. M is the molarity of monovalent cations, % GC is the percentage of guanosine and cytosine nucleotides in the DNA, % form is the percentage of formamide in the hybridization solution, and L is the length of the hybrid in base pairs. Tm is reduced by about 1° C. for each 1% of mismatching; thus, Tm, hybridization, and/or wash conditions can be adjusted to hybridize to sequences of the desired identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. Generally, highly stringent hybridization and wash conditions are selected to be about 5° C. lower than the thermal melting point (Tm) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide In general, a signal to noise ratio of 2× (or higher) than that observed for an unrelated probe in the particular hybridization assay indicates detection of a specific hybridization.

Very stringent conditions are selected to be equal to the Tm for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

Agents

The agent disclosed herein can be any agent that is capable of linking to the nucleic acid aptamer. This link can be covalent or non-covalent. Chemistries that can be used to link molecules to the aptamer are known in the art, such as disulfide linkages, amino linkages, covalent linkages, etc. The agent disclosed herein can optionally link with more than one aptamer. For example, the agent can link with 2, 3, 4, 5, 6, 7, 8, 9, 10, or more aptamers.

The agents disclosed herein can include, for example, therapeutic, diagnostic, and/or prophylactic agents. Exemplary agents to be delivered in accordance with the present invention include, but are not limited to, small molecules, organometallic compounds, nucleic acids (such as siRNA and RNAi), proteins (including multimeric proteins, protein complexes, etc.), peptides, lipids, carbohydrates, hormones, metals, radioactive elements and compounds, gelonins, phototoxic agents, drugs, vaccines, immunological agents, etc., and/or combinations thereof. Specifically, the agent can be a chemotherapeutic agent, such as methotrexate.

The agent can be a therapeutic agent. The therapeutic agent to be delivered may be a mixture of pharmaceutically active agents. For example, a local anesthetic may be delivered in combination with an anti-cancer agent, such as methotrexate. To give another example, an antibiotic may be combined with an inhibitor of the enzyme commonly produced by bacteria to inactivate the antibiotic (e.g., penicillin and clavulanic acid). The therapeutic agent can specifically target CD117. For example, specific binding of the nucleic acid to a protein of CD117 can result in delivery of the therapeutic agent to CD117. The therapeutic agent can then cause apoptosis of the CD117 cell.

Examples of therapeutic agents which can be used include, but are not limited to an antagonist of fibroblast-growth factor (FGF), hepatocyte growth factor (HGF), tissue factor (TF), protein C, protein S, platelet-derived growth factor (PDGF), heregulin, macrophage-stimulating protein (MSP) or vascular endothelial growth factor (VEGF), or an antagonist of a receptor for epidermal-growth factor (EGF), fibroblast-growth factor (FGF), hepatocyte growth factor (HGF), tissue factor (TF), protein C, protein S, platelet-derived growth factor (PDGF), heregulin, macrophage-stimulating protein (MSP), or vascular endothelial growth factor (VEGF), including HER2 receptor, HER3 receptor, c-MET, and other receptor tyrosine kinases.

The agent to be delivered can be a mixture of anti-cancer agents. The conjugates can be administered in combination with one or more of the anti-cancer agents described herein. To provide an example, conjugates comprising an anti-cancer agent to be delivered are administered in combination with hormonal therapy. The growth of some types of tumors can be inhibited by providing or blocking certain hormones. For example, steroids (e.g. dexamethasone) can inhibit tumor growth or associated edema and may cause regression of lymph node malignancies A. Small Molecule Agents In some embodiments, the agent to be delivered is a small molecule and/or organic compound with pharmaceutical activity. In some embodiments, the agent is a clinically-used drug. In some embodiments, the drug is an anti-cancer agent, antibiotic, antiviral agent, anti-HIV agent, anti-parasite agent, anti-protozoal agent, anesthetic, anticoagulant, inhibitor of an enzyme, steroidal agent, steroidal or non-steroidal antiinflammatory agent, antihistamine, immunosuppressant agent, anti-neoplastic agent, antigen, vaccine, antibody, decongestant, sedative, opioid, analgesic, anti-pyretic, birth control agent, hormone, prostaglandin, progestational agent, anti-glaucoma agent, ophthalmic agent, anticholinergic, analgesic, anti-depressant, anti-psychotic, neurotoxin, hypnotic, tranquilizer, anti-convulsant, muscle relaxant, anti-Parkinson agent, anti-spasmodic, muscle contractant, channel blocker, miotic agent, anti-secretory agent, antithrombotic agent, anticoagulant, anticholinergic, β-adrenergic blocking agent, diuretic, cardiovascular active agent, vasoactive agent, vasodilating agent, anti-hypertensive agent, angiogenic agent, modulators of cell-extracellular matrix interactions (e.g. cell growth inhibitors and anti-adhesion molecules), inhibitors of DNA, RNA, or protein synthesis, etc.

The therapeutic agent to be delivered can be an anti-cancer agent (i.e. cytotoxic agents). Most anti-cancer agents can be divided in to the following categories: alkylating agents, antimetabolites, natural products, and hormones and antagonists. An example includes methotrexate.

Anti-cancer agents typically affect cell division and/or DNA synthesis. However, some chemotherapeutic agents do not directly interfere with DNA. To give but one example, tyrosine kinase inhibitors (imatinib mesylate/Gleevec®) directly target a molecular abnormality in certain types of cancer (chronic myelogenous leukemia, gastrointestinal stromal tumors, etc.).

Alkylating agents are so named because of their ability to add alkyl groups to many electronegative groups under conditions present in cells. Alkylating agents typically function by chemically modifying cellular DNA. Exemplary alkylating agents include nitrogen mustards (e.g. mechlorethamine, cyclophosphamide, ifosfamide, melphalan (1-sarcolysin), chlorambucil), ethylenimines and methylmelamines (e.g. altretamine (hexamethylmelamine; HMM), thiotepa (Methylene thiophosphoramide), triethylenemelamine (TEM)), alkyl sulfonates (e.g. busulfan), nitrosureas (e.g. carmustine (BCNU), lomustine (CCMU), semustine (methyl-CCNU), streptozocin (streptozotocin)), and triazenes (e.g. dacarbazine (DTIC; dimethyltriazenoimidazolecarboxamide)).

Antimetabolites act by mimicking small molecule metabolites (e.g. folic acid, pyrimidines, and purines) in order to be incorporated into newly synthesized cellular DNA. Such agents also affect RNA synthesis. An exemplary folic acid analog is methotrexate (amethopterin). Exemplary pyrimidine analogs include fluorouracil (5-fluorouracil; 5-FU), floxuridine (fluorodeoxyuridine; FUdR), and cytarabine (cytosine arabinoside). Exemplary purine analogs include mercaptopurine (6-mercaptopurine; 6-MP), azathioprine, thioguanine (6-thioguanine; TG), fludarabine phosphate, pentostatin (2'-deoxycoformycin), cladribine (2-chlorodeoxyadenosine; 2-CdA), and erythrohydroxynonyladenine (EHNA).

Natural small molecule products which can be used as anti-cancer agents include plant alkaloids and antibiotics. Plant alkaloids and terpenoids (e.g. *vinca* alkaloids, podophyllotoxin, taxanes, etc.) typically block cell division by preventing microtubule function. *Vinca* alkaloids (e.g. vincristine, vinblastine (VLB), vinorelbine, vindesine, etc.) bind to tubulin and inhibit assembly of tubulin into microtubules. *Vinca* alkaloids are derived from the Madagascar periwinkle, *Catharanthus roseus* (formerly known as *Vinca rosea*). Podophyllotoxin is a plant-derived compound used to produce two other cytostatic therapeutic agents, etoposide and teniposide, which prevent cells from entering the Gl and S phases of the cell cycle. Podophyllotoxin is primarily obtained from the American Mayapple (*Podophyllum peltatum*) and a Himalayan Mayapple (*Podophyllum hexandrum*). Taxanes (e.g. paclitaxel, docetaxel, etc.) are derived from the Yew Tree. Taxanes enhance stability of microtubules, preventing the separation of chromosomes during anaphase.

Antibiotics which can be used as anti-cancer agents include dactinomycin (actinomycin D), daunorubicin (daunomycin; rubidomycin), doxorubicin, idarubicin, bleomycin, plicamycin (mithramycin), and mitomycin (mytomycin C).

Other small molecules which can be used as anti-cancer agents include platinum coordination complexes (e.g. cisplatin (cω-DDP), carboplatin), anthracenedione (e.g. mitoxantrone), substituted urea (e.g. hydroxyurea), methylhydrazine derivatives (e.g. procarbazine (N-methylhydrazine, MIH), and adrenocortical suppressants (e.g. mitotane (o,p'-DDD), aminoglutethimide).

Hormones which can be used as anti-cancer agents include adrenocorticosteroids (e.g. prednisone), aminoglutethimide, progestins (e.g. hydroxyprogesterone caproate, medroxyprogesterone acetate, megestrol acetate), estrogens (e.g. diethylstilbestrol, ethinyl estradiol), antiestrogen (e.g. tamoxifen), androgens (e.g. testosterone propionate, fluoxymesterone), antiandrogens (e.g. flutamide), and gonadotropin-releasing hormone analog (e.g. leuprolide).

Topoisomerase inhibitors act by inhibiting the function of topoisomerases, which are enzymes that maintain the topology of DNA. Inhibition of type I or type II topoisomerases interferes with both transcription and replication of DNA by upsetting proper DNA supercoiling. Some exemplary type I topoisomerase inhibitors include camptothecins (e.g. irinotecan, topotecan, etc.). Some exemplary type II topoisomerase inhibitors include amsacrine, etoposide, etoposide phosphate, teniposide, etc., which are semisynthetic derivatives of epipodophyllotoxins, discussed herein.

B. Nucleic Acid Agents

The conjugates disclosed herein can be used to deliver one or more nucleic acids (e.g. functional RNAs, functional DNAs, etc.) to a specific location such as an organ, tissue, cell, extracellular matrix component, and/or intracellular compartment.

In general, a "functional RNA" is an RNA that does not code for a protein but instead belongs to a class of RNA molecules whose members characteristically possess one or more different functions or activities within a cell. It will be appreciated that the relative activities of functional RNA molecules having different sequences may differ and may depend at least in part on the particular cell type in which the RNA is present. Thus the term "functional RNA" is used herein to refer to a class of RNA molecule and is not intended to imply that all members of the class will in fact display the activity characteristic of that class under any particular set of conditions. In some embodiments, functional RNAs include RNAi-inducing entities (e.g. short interfering RNAs (siRNAs), short hairpin RNAs (shRNAs), and microRNAs), ribozymes, tRNAs, rRNAs, RNAs useful for triple helix formation, etc.

RNAi is an evolutionarily conserved process in which presence of an at least partly double-stranded RNA molecule in a eukaryotic cell leads to sequence-specific inhibition of gene expression. RNAi was originally described as a phenomenon in which the introduction of long dsRNA (typically hundreds of nucleotides) into a cell results in degradation of mRNA containing a region complementary to one strand of the dsRNA (U.S. Pat. No. 6,506,559; and Fire et al., 1998, Nature, 391:806). Subsequent studies in *Drosophila* showed that long dsRNAs are processed by an intracellular RNase Ill-like enzyme called Dicer into smaller dsRNAs primarily comprised of two approximately 21 nucleotide (nt) strands that form a 19 base pair duplex with 2 nt 3' overhangs at each end and 5'-phosphate and 3'-hydroxyl groups (see, e.g., PCT Publication WO 01/75164;

U.S. Patent Application Publications 2002/0086356 and 2003/0108923; Zamore et al, 2000, Cell, 101:25; and Elbashir of al., 2001, Genes Dev., 15:188).

Short dsRNAs having structures such as this, referred to as siRNAs, silence expression of genes that include a region that is substantially complementary to one of the two strands. This strand is referred to as the "antisense" or "guide" strand, with the other strand often being referred to as the "sense" strand. The siRNA is incorporated into a ribonucleoprotein complex termed the RNA-induced silencing complex (RISC) that contains member(s) of the Argonaute protein family. Following association of the siRNA with RISC, a helicase activity unwinds the duplex, allowing an alternative duplex to form the guide strand and a target mRNA containing a portion substantially complementary to the guide strand. An endonuclease activity associated with the Argonaute protein(s) present in RISC is responsible for "slicing" the target mRNA, which is then further degraded by cellular machinery.

It will be appreciated that molecules having the appropriate structure and degree of complementarity to a target gene will exhibit a range of different silencing efficiencies. A variety of additional design criteria have been developed to assist in the selection of effective siRNA sequences. Numerous software programs that can be used to choose siRNA sequences that are predicted to be particularly effective to silence a target gene of choice are available (see, e.g., Yuan et al., 2004, Nucl. Acids. Res., 32:W130; and Santoyo et al, 2005, Bioinformatics, 21: 1376).

As will be appreciated by one of ordinary skill in the art, RNAi may be effectively mediated by RNA molecules having a variety of structures that differ in one or more respects from that described above. For example, the length of the duplex can be varied (e.g., from about 17-29 nucleotides); the overhangs need not be present and, if present, their length and the identity of the nucleotides in the overhangs can vary (though most commonly symmetric dTdT overhangs are employed in synthetic siRNAs).

Additional structures, referred to as short hairpin RNAs (shRNAs), are capable of mediating RNA interference. An shRNA is a single RNA strand that contains two complementary regions that hybridize to one another to form a double-stranded "stem," with the two complementary regions being connected by a single-stranded loop. shRNAs are processed intracellularly by Dicer to form an siRNA structure containing a guide strand and an antisense strand. While shRNAs can be delivered exogenously to cells, more typically intracellular synthesis of shRNA is achieved by introducing a plasmid or vector containing a promoter operably linked to a template for transcription of the shRNA into the cell, e.g., to create a stable cell line or transgenic organism.

While sequence-specific cleavage of target mRNA is currently the most widely used means of achieving gene silencing by exogenous delivery of short RNAi entities to cells, additional mechanisms of sequence-specific silencing mediated by short RNA entities are known. For example, post-transcriptional gene silencing mediated by small RNA entities can occur by mechanisms involving translational repression. Certain endogenously expressed RNA molecules form hairpin structures containing an imperfect duplex portion in which the duplex is interrupted by one or more mismatches and/or bulges. These hairpin structures are processed intracellularly to yield single-stranded RNA species referred to as known as microRNAs (miRNAs), which mediate translational repression of a target transcript to which they hybridize with less than perfect complementarity. siRNA-like molecules designed to mimic the structure of miRNA precursors have been shown to result in translational repression of target genes when administered to mammalian cells.

A short RNAi entity that is delivered according to the methods of the invention and/or is present in a composition of the invention may be designed to silence any eukaryotic gene. The gene can be a mammalian gene, e.g., a human gene. The gene can be a wild type gene, a mutant gene, an allele of a polymorphic gene, etc. The gene can be disease-associated, e.g., a gene whose overexpression, under-expression, or mutation is associated with or contributes to development or progression of a disease. For example, the gene can be oncogene. The gene can encode a receptor or putative receptor for an infectious agent such as a virus (see, e.g., Dykxhhorn et al., 2003, Nat. Rev. Mol. Cell Biol, 4:457 for specific examples).

The nucleic acid agent can also be a ribozyme. A ribozyme is designed to catalytically cleave target mRNA transcripts may be used to prevent translation of a target mRNA and/or expression of a target (see, e.g., PCT publication WO 90/11364; and Sarver et al., 1990, Science 247:1222). Endogenous target gene expression may be reduced by targeting deoxyribonucleotide sequences complementary to the regulatory region of the target gene (i.e., the target gene's promoter and/or enhancers) to form triple helical structures that prevent transcription of the target gene in target muscle cells in the body (see generally, Helene, 1991, Anticancer Drug Des. 6:569; Helene et al, 1992, Ann, N.Y. Acad. Sci. 660:27; and Maher, 1992, Bioassays 14:807).

C. Protein Agents

The agent to be delivered can be a protein or peptide. In certain embodiments, peptides range from about 5 to about 5000, 5 to about 1000, about 5 to about 750, about 5 to about 500, about 5 to about 250, about 5 to about 100, about 5 to about 75, about 5 to about 50, about 5 to about 40, about 5 to about 30, about 5 to about 25, about 5 to about 20, about 5 to about 15, or about 5 to about 10 amino acids in size. Peptides from panels of peptides comprising random sequences and/or sequences which have been varied consistently to provide a maximally diverse panel of peptides may be used.

The terms "protein," "polypeptide," and "peptide" are used interchangeably herein, typically referring to a polypeptide having a length of less than about 500 to about 1000 amino acids. Polypeptides may contain L-amino acids, D-amino acids, or both and may contain any of a variety of amino acid modifications or analogs known in the art. Useful modifications include, e.g., terminal acetylation, amidation, etc. In some embodiments, polypeptides may comprise natural amino acids, unnatural amino acids, synthetic amino acids, and combinations thereof, as described herein.

The agent to be delivered may be a peptide, hormone, erythropoietin, insulin, cytokine, antigen for vaccination, etc. In some embodiments, the agent to be delivered may be an antibody and/or characteristic portion thereof. In some embodiments, antibodies may include, but are not limited to, polyclonal, monoclonal, chimeric (i.e. "humanized"), single chain (recombinant) antibodies. In some embodiments, antibodies may have reduced effector functions and/or bispecific molecules. In some embodiments, antibodies may include Fab fragments and/or fragments produced by a Fab expression library, as described in further detail above.

D. Carbohydrate Agents

The agent to be delivered can be a carbohydrate, such as a carbohydrate that is associated with a protein (e.g. glycoprotein, proteogycan, etc.). A carbohydrate may be natural or synthetic. A carbohydrate may also be a derivatized natural carbohydrate. In certain embodiments, a carbohydrate may be a simple or complex sugar. In certain embodiments, a carbohydrate is a monosaccharide, including but not limited to glucose, fructose, galactose, and ribose. In certain embodiments, a carbohydrate is a disaccharide, including but not limited to lactose, sucrose, maltose, trehalose, and cellobiose. In certain embodiments, a carbohydrate is a polysaccharide, including but not limited to cellulose, microcrystalline cellulose, hydroxypropyl methylcellulose (HPMC), methylcellulose (MC), dextrose, dextran, glycogen, xanthan gum, gellan gum, starch, and pullulan. In certain embodiments, a carbohydrate is a sugar alcohol, including but not limited to mannitol, sorbitol, xylitol, erythritol, malitol, and lactitol.

E. Lipid Agents

The agent to be delivered can be a lipid, such as a lipid that is associated with a protein (e.g. lipoprotein). Exemplary lipids that may be used in accordance with the present invention include, but are not limited to, oils, fatty acids, saturated fatty acid, unsaturated fatty acids, essential fatty acids, cis fatty acids, trans fatty acids, glycerides, monoglycerides, diglycerides, triglycerides, hormones, steroids (e.g., cholesterol, bile acids), vitamins (e.g. vitamin E), phospholipids, sphingolipids, and lipoproteins.

In some embodiments, the lipid may comprise one or more fatty acid groups or salts thereof. In some embodiments, the fatty acid group may comprise digestible, long chain (e.g., $C_8$-$C_{50}$), substituted or unsubstituted hydrocarbons. In some embodiments, the fatty acid group may be a $C_{10}$-$C_{20}$ fatty acid or salt thereof. In some embodiments, the fatty acid group may be a $C_{15}$-$C_{20}$ fatty acid or salt thereof. In some embodiments, the fatty acid group may be a $C_{15}$-$C_{25}$ fatty acid or salt thereof. In some embodiments, the fatty acid group may be unsaturated. In some embodiments, the fatty acid group may be monounsaturated. In some embodiments, the fatty acid group may be polyunsaturated. In some embodiments, a double bond of an unsaturated fatty acid group may be in the cis conformation. In some embodiments, a double bond of an unsaturated fatty acid may be in the trans conformation.

In some embodiments, the fatty acid group may be one or more of butyric, caproic, caprylic, capric, lauric, myristic, palmitic, stearic, arachidic, behenic, or lignoceric acid. In some embodiments, the fatty acid group may be one or more of palmitoleic, oleic, vaccenic, linoleic, alpha-linolenic, gamma-linoleic, arachidonic, gadoleic, arachidonic, eicosapentaenoic, docosahexaenoic, or erucic acid.

F. Diagnostic Agents

The agent to be delivered can be a diagnostic agent. In some embodiments, diagnostic agents include gases; commercially available imaging agents used in positron emissions tomography (PET), computer assisted tomography (CAT), single photon emission computerized tomography, x-ray, fluoroscopy, and magnetic resonance imaging (MRI); anti-emetics; and contrast agents. Examples of suitable materials for use as contrast agents in MM include gadolinium chelates, as well as iron, magnesium, manganese, copper, and chromium. Examples of materials useful for CAT and x-ray imaging include iodine-based materials.

In some embodiments, the conjugate can comprise a diagnostic agent used in magnetic resonance imaging (MM), such as iron oxide particles or gadolinium complexes. Gadolinium complexes that have been approved for clinical use include gadolinium chelates with DTPA, DTPA-BMA, DOTA and HP-DO3 A.

The conjugate can comprise radionuclides as therapeutic and/or diagnostic agents. Among the radionuclides used, gamma-emitters, positron-emitters, and X-ray emitters are suitable for diagnostic and/or therapy, while beta emitters and alpha-emitters may also be used for therapy. Suitable radionuclides for forming the conjugate include, but are not limited to, 123I, 125I, 130I, 131I, 133I, 135I, 47Sc, 72As, 72Se, 90Y, 88Y, 97Ru, 100Pd, 101mRh, 119Sb, 128Ba, 197Hg, 211At, 212Bi, 212Pb, 109Pd, 111In, 67Ga, 68Ga, 67Cu, 75Br, 77Br, "mTc, 14C, 13N, 150, 32P, 33P, and 18F.

A diagnostic agent can be a fluorescent, luminescent, or magnetic moiety. For example, a detectable moiety such as a fluorescent or luminescent dye, etc., can be entrapped, embedded, or encapsulated by a particle core and/or coating layer.

Fluorescent and luminescent moieties include a variety of different organic or inorganic small molecules commonly referred to as "dyes," "labels," or "indicators." Examples include fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase, aequorin and derivatives thereof. Numerous fluorescent and luminescent dyes and proteins are known in the art (see, e.g., U.S. Patent Application Publication 2004/0067503; Valeur, B., "Molecular Fluorescence: Principles and Applications," John Wiley and Sons, 2002; Handbook of Fluorescent Probes and Research Products, Molecular Probes, 9th edition, 2002; and The Handbook—A Guide to Fluorescent Probes and Labeling Technologies, Invitrogen, 10th edition, available at the Invitrogen web site).

G. Prophylactic Agents

The agent to be delivered can be a prophylactic agent. In some embodiments, prophylactic agents include vaccines. Vaccines may comprise isolated proteins or peptides, inactivated organisms and viruses, dead organisms and virus, genetically altered organisms or viruses, and cell extracts. Prophylactic agents may be combined with interleukins, interferon, cytokines, and adjuvants such as cholera toxin, alum, Freund's adjuvant, etc. Prophylactic agents may include antigens of such bacterial organisms as *Streptococcus pnuemoniae, Haemophilus influenzae, Staphylococcus aureus, Streptococcus pyrogenes, Corynebacterium diphtherias, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; antigens of such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as *Cryptococcus neoformans, Histoplasma capsulatum, Candida albicans, Candida tropicalis, Nocardia asteroides, Rickettsia ricketsii, Rickettsia*

*typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

H. Nutraceutical Agents

The therapeutic agent to be delivered can be a nutraceutical agent. In some embodiments, the nutraceutical agent provides basic nutritional value, provides health or medical benefits, and/or is a dietary supplement. In some embodiments, the nutraceutical agent is a vitamin (e.g. vitamins A, B, C, D, E, K, etc.), mineral (e.g. iron, magnesium, potassium, calcium, etc.), or essential amino acid (e.g. lysine, glutamine, leucine, etc.).

Nutraceutical agents can include plant or animal extracts, such as fatty acids and/or omega-3 fatty acids (e.g. DHA or ARA), fruit and vegetable extracts, lutein, phosphatidylserine, lipoid acid, melatonin, glucosamine, chondroitin, aloe vera, guggul, green tea, lycopene, whole foods, food additives, herbs, phytonutrients, antioxidants, flavonoid constituents of fruits, evening primrose oil, flaxseeds, fish and marine animal oils (e.g. cod liver oil), and probiotics.

Exemplary nutraceutical agents and dietary supplements are disclosed, for example, in Roberts et al., (Nutraceuticals: The Complete Encyclopedia of Supplements, Herbs, Vitamins, and Healing Foods, American Nutraceutical Association, 2001). Nutraceutical agents and dietary supplements are also disclosed in Physicians ' Desk Reference for Nutritional Supplements, 1st Ed. (2001) and The Physicians' Desk Reference or Herbal Medicines, 1st Ed. (2001).

Those skilled in the art will recognize that this is an exemplary, not comprehensive, list of therapeutic or diagnostic agents that can be delivered using the conjugates disclosed herein. Any therapeutic or diagnostic agent may be associated with conjugates for targeted delivery as disclosed herein.

Pharmaceutical Compositions

Disclosed herein are pharmaceutical compositions, wherein the composition comprises conjugates comprising one or more nucleic acid aptamers and a therapeutically effective amount of one or more agents. For example, the aptamer can comprise 2, 3, 4, or 5 or more agents. Disclosed herein are nucleic acid aptamers and agents; and one or more pharmaceutically acceptable excipients. Also disclosed is a method of administering a pharmaceutical composition comprising a conjugate of a nucleic acid aptamer and an agent to a subject in need thereof is provided.

The phrase "active ingredient" generally refers to a conjugate comprising a nucleic acid aptamer and an agent, as described herein.

The formulations of the pharmaceutical compositions described herein may be prepared by any method known or hereafter developed in the art of pharmaceutics. In general, such preparatory methods include the step of bringing the active ingredient into association with one or more excipients and/or one or more other accessory ingredients, and then, if necessary and/or desirable, shaping and/or packaging the product into a desired single- or multi-dose unit.

The pharmaceutical composition can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable excipient(s), and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations can additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro, (Lippincott, Williams & Wilkins, Baltimore, Md., 2006) discloses various excipients used in formulating pharmaceutical compositions and known techniques for the preparation thereof.

The pharmaceutically acceptable excipient can be at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxy ethylene sorbitan [Tween 60], polyoxy ethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, polyvinylpyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytouened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include, but are not limited to, pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and perfuming agents. In certain embodiments for parenteral administration, conjugates can be mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions, may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U. S. P. and isotonic sodium chloride solution, etc. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the active ingredient then depends upon its rate of dissolution which, in turn, may depend upon crystal size and crystalline form. In some embodiments, delayed absorption of a parenterally administered active ingredient is accomplished by dissolving or suspending the drug in an oil vehicle.

Compositions for rectal or vaginal administration are typically suppositories which can be prepared by mixing the conjugates with suitable non-irritating excipients such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and micro crystalline cellulose. In the case of capsules, tablets and pills, the dosage forms may comprise buffering agents. Examples of embedding compositions which can be used include polymeric substances and waxes.

Dosage forms for topical and/or transdermal administration of a conjugate may include ointments, pastes, creams, lotions, gels, powders, solutions, sprays, inhalants and/or patches. Generally, the active component is admixed under sterile conditions with a pharmaceutically acceptable excipient and/or any needed preservatives and/or buffers as may be required. Additionally, the present invention contemplates the use of transdermal patches, which often have the added advantage of providing controlled delivery of an active ingredient to the body. Such dosage forms may be prepared, for example, by dissolving and/or dispensing the active ingredient in the proper medium. Alternatively or additionally, the rate may be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649, 912; 5,569,189; 5,704,911; 5,383,851; 5,893,397; 5,466, 220; 5,339,163; 5,312,335; 5,503,627; 5,064,413; 5,520, 639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the excipients and/or additional ingredients described herein.

The pharmaceutical composition can be prepared, packaged, and/or sold in a formulation suitable for pulmonary administration via the buccal cavity. Such a formulation may comprise dry particles which comprise the active ingredient and which have a diameter in the range from about 0.5 μm to about 7 μm or from about 1 μm to about 6 μm. Such compositions are conveniently in the form of dry powders for administration using a device comprising a dry powder reservoir to which a stream of propellant may be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 μm and at least 95% of the particles by number have a diameter less than 7 μm. Alternatively, at least 95% of the particles by weight have a diameter greater than 1 μm and at least 90% of the particles by number have a diameter less than 6 μm. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 μm to about 200 μm.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 μm to 500 μm. Such a formulation is administered in the manner in which snuff is taken, i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may comprise one or more of the excipients and/or additional ingredients described herein. A pharmaceutical composition of the invention may be prepared, packaged, and/or sold in a formulation suitable for buccal administration. Such formulations may, for example, be in the form of tablets and/or lozenges made using conventional methods, and may, for example, 0.1% to 20% (w/w) active ingredient, the balance comprising an orally dissolvable and/or degradable composition and, optionally, one or more of the excipients and/or additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 μm to about 200 μm, and may further comprise one or more of the excipients and/or additional ingredients described herein.

A pharmaceutical composition of the invention may be prepared, packaged, and/or sold in a formulation suitable for ophthalmic administration. Such formulations may, for example, be in the form of eye drops including, for example, a 0.1%/1.0% (w/w) solution and/or suspension of the active ingredient in an aqueous or oily liquid excipient. Such drops may further comprise buffering agents, salts, and/or one or more other of the excipients and/or additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in Remington: The Science and Practice of Pharmacy 21st ed., Lippincott Williams & Wilkins, 2005.

Administration

A therapeutically effective amount of the disclosed conjugates can be delivered to a patient and/or organism prior to, simultaneously with, and/or after diagnosis with a disease, disorder, and/or condition e.g. cancer). In some embodiments, a therapeutic or diagnostic amount of a conjugate is delivered to a patient and/or organism prior to, simultaneously with, and/or after onset of symptoms of a disease, disorder, and/or condition. In some embodiments, the amount of conjugate is sufficient to treat, alleviate, ameliorate, relieve, delay onset of, inhibit progression of, reduce severity of, and/or reduce incidence of one or more symptoms or features of the disease, disorder, and/or condition.

The compositions, according to the method of the present invention, may be administered using any amount and any route of administration effective for treatment. The exact amount required will vary from subject to subject, depending on the species, age, and general condition of the subject, the severity of the infection, the particular composition, its mode of administration, its mode of activity, and the like. The compositions of the invention are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disorder being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The pharmaceutical compositions disclosed herein can be administered by any route. In some embodiments, the pharmaceutical compositions of the present invention are administered by a variety of routes, including oral, intravenous, intramuscular, intraarterial, intramedullary, intrathecal, subcutaneous, intraventricular, transdermal, interdermal, rectal, intravaginal, intraperitoneal, topical (as by powders, ointments, creams, and/or drops), transdermal, mucosal, nasal, buccal, enteral, sublingual; by intratracheal instillation, bronchial instillation, and/or inhalation; and/or as an oral spray, nasal spray, and/or aerosol. Specifically contemplated routes are systemic intravenous injection, regional administration via blood and/or lymph supply, and/or direct administration to an affected site. The conjugates can be administered parenterally, intravenously, or orally, for example.

The disclosed compositions can be administered directly to an affected site. For example, the conjugates can be administered locally near a tumor and/or may be administered directly to a tumor. In some embodiments, local administration refers to administration of conjugates directly to a specific organ. In some embodiments, local administration refers to administration of conjugates directly to a particular organ, tissue, and/or cell. Local administration may be achieved via injection of conjugates directly into a tumor or in the vicinity of a tumor. Local administration may be achieved by topical administration of conjugates at or near the site of a tumor. Local administration may be achieved by implantation of conjugates at or near a site of a tumor by stereotactic surgery. Local administration may be achieved by implantation of conjugates at or near the site of a tumor during surgical removal of the tumor. In some embodiments, local administration refers to administration of the disclosed conjugates to a specific cell or population of cells.

In general the most appropriate route of administration will depend upon a variety of factors including the nature of the agent (e.g., its stability in the environment of the gastrointestinal tract), the condition of the subject (e.g., whether the subject is able to tolerate oral administration), etc. However, the invention encompasses the delivery of the conjugates by any appropriate route taking into consideration likely advances in the sciences of drug delivery.

The disclosed conjugates can be administered at therapeutic agent in amounts ranging from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

Combination Therapy

Disclosed herein are "therapeutic cocktails" comprising the conjugates disclosed herein. Conjugates can comprise a single nucleic acid aptamer which can bind to multiple targets, i.e., different cells or different proteins on the same cell. Also disclosed are different nucleic acid aptamers, and all of the different nucleic acid aptamers can bind to the same target, i.e., the same protein on the same cell, or different proteins on the same cell. Also disclosed are nucleic acid aptamers that interact with different targets. These different targets can be associated with the same cell type, such as CD117. Alternatively, different targets can be associated with different cell types.

It will be appreciated that conjugates of the present invention can be employed in combination therapies. The particular combination of therapies (therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, a conjugate useful for detecting tumors can be administered concurrently with another agent useful for detecting tumors), or they may achieve different effects (one conjugate useful for detecting tumors, and another useful for treating tumors).

The pharmaceutical compositions disclosed herein can be administered either alone or in combination with one or more other therapeutic agents. By "in combination with," it is not intended to imply that the agents must be administered at the same time and/or formulated for delivery together, although these methods of delivery are within the scope of the invention. The compositions can be administered concurrently with, prior to, or subsequent to, one or more other desired therapeutics or medical procedures. In general, each agent will be administered at a dose and/or on a time schedule determined for that agent. Additionally, the invention encompasses the delivery of pharmaceutical compositions in combination with agents that may improve their bioavailability, reduce and/or modify their metabolism, inhibit their excretion, and/or modify their distribution within the body.

The particular combination of therapies (therapeutics and/or procedures) to employ in a combination regimen will take into account compatibility of the desired therapeutics and/or procedures and/or the desired therapeutic effect to be achieved. It will be appreciated that the therapies employed may achieve a desired effect for the same disorder (for example, a conjugate or nucleic acid aptamer) may be administered concurrently with another therapeutic agent used to treat the same disorder), and/or they may achieve different effects (e.g., control of any adverse effects). Conjugates can be administered with a second therapeutic agent that is approved by the U.S. Food and Drug Administration. Therapeutically active agents utilized in combination can be administered together in a single composition or administered separately in different compositions. In general, it is expected that agents utilized in combination with be utilized at levels that do not exceed the levels at which they are utilized individually. In some embodiments, the levels utilized in combination will be lower than those utilized individually.

The conjugates disclosed herein can be administered in combination with any therapeutic agent or therapeutic regimen that is useful to treat, alleviate, ameliorate, relieve, delay onset of, inhibit progression of, reduce severity of, and/or reduce incidence of one or more symptoms or features of cancer. For example, the disclosed conjugates can be administered in combination with traditional cancer therapies including, but not limited to, surgery, chemotherapy, radiation therapy, hormonal therapy, immunotherapy, complementary or alternative therapy, and any combination of these therapies.

The disclosed conjugates can be administered in combination with surgery to remove a tumor. Because complete removal of a tumor with minimal or no damage to the rest of a patient's body is typically the goal of cancer treatment, surgery is often performed to physically remove part or all of a tumor. If surgery is unable to completely remove a tumor, additional therapies (e.g. chemotherapy, radiation therapy, hormonal therapy, immunotherapy, complementary or alternative therapy) can be employed.

The conjugates can be administered in combination with radiation therapy. Radiation therapy (also known as radiotherapy, X-ray therapy, or irradiation) is the use of ionizing radiation to kill cancer cells and shrink tumors. Radiation therapy can be used to treat almost any type of solid tumor, including cancers of the brain, breast, cervix, larynx, lung, pancreas, prostate, skin, stomach, uterus, or soft tissue sarcomas. Radiation can be used to treat leukemia and lymphoma. Radiation therapy can be administered externally via external beam radiotherapy (EBRT) or internally via brachytherapy. Typically, the effects of radiation therapy are localized and confined to the region being treated. Radiation therapy injures or destroys tumor cells in an area being treated (e.g. a target organ, tissue, and/or cell) by damaging their genetic material, preventing tumor cells from growing and dividing. In general, radiation therapy attempts to damage as many tumor cells as possible while limiting harm to nearby healthy organs, tissues, and/or cells. Hence, it is often administered in multiple doses, allowing healthy organs, tissues, and/or cells to recover between fractions.

The disclosed conjugates can be administered in combination with immunotherapy. Immunotherapy is the use of immune mechanisms against tumors which can be used in various forms of cancer, such as breast cancer (e.g. trastuzumab/HERCEPTIN™), leukemia (e.g. gemtuzumab ozogamicin/MYLOTARG™), and non-Hodgkin's lymphoma (e.g. rituximab/RITUXAN™). In some embodiments, immunotherapy agents are monoclonal antibodies directed against proteins that are characteristic to the cells of the cancer in question. In some embodiments, immunotherapy agents are cytokines that modulate the immune system's response. In some embodiments, immunotherapy agents may be vaccines.

Vaccines can also be administered to prevent and/or delay the onset of cancer. In some embodiments, cancer vaccines prevent and/or delay the onset of cancer by preventing infection by oncogenic infectious agents. In some embodiments, cancer vaccines prevent and/or delay the onset of cancer by mounting an immune response against cancer-specific epitopes.

The conjugates which are administered in combination with any of the traditional cancer treatments described herein may be also be administered in combination with any therapeutic agent or therapeutic regimen that is useful to treat, alleviate, ameliorate, relieve, delay onset of, inhibit progression of, reduce severity of, and/or reduce incidence of one or more side effects of cancer treatment. To give but a few examples, pain can be treated with opioids and/or analgesics (e.g. morphine, oxycodone, antiemetics, etc.); nausea and vomiting can be treated with 5-HT3 inhibitors (e.g. dolasetron/ANZEMET™, granisetron/KYTRIL™, ondansetron/ZOFRAN™, palonsetron/ALOXI™) and/or substance P inhibitors (e.g. aprepitant/EMEND™); immunosuppression can be treated with a blood transfusion; infection and/or sepsis can be treated with antibiotics (e.g. penicillins, tetracyclines, cephalosporins, sulfonamides, aminoglycosides, etc.); and so forth.

In addition to the conjugates described above that are useful for simultaneously diagnosing and treating cancer, the conjugates can be administered and/or diagnostic methods may be performed in combination with (e.g. in parallel with) any therapeutic or diagnostic agent or regimen that is useful to diagnose one or more symptoms or features of cancer (e.g. detect the presence of and/or locate a tumor). The conjugates can be used in combination with one or more other diagnostic agents. For example, the conjugates can be used to detect tumors, and can be administered in combination with other agents useful in the detection of tumors. For example, conjugates can be administered in combination with traditional tissue biopsy followed by immunohistochemical staining and serological tests. Alternatively or additionally, the conjugates can be administered in combination with a contrasting agent for use in computed tomography (CT) scans and/or MRI.

Methods of Treatment

Disclosed herein are methods of targeting CD117 cells with an agent, the method comprising conjugating a nucleic acid aptamer comprising a region that interacts with a CD117 cell to the agent, and exposing CD117 cells to the aptamer/agent-conjugate. The aptamer can comprise a nucleic acid, such as those found in SEQ ID NO: 1 or SEQ ID NO: 4 or SEQ ID NO: 5 or SEQ ID NO: 6, for example. The conjugates that can be used with this method are described herein.

Also disclosed are methods of treating a subject with cancer, the method comprising: identifying a subject in need of treatment for cancer, and administering a pharmaceutical composition to the subject, wherein the pharmaceutical composition comprises a conjugate of a nucleic acid aptamer and a cancer treating agent, wherein the nucleic acid aptamer comprises a region that interacts with a CD117 cell, thereby treating cancer in the subject. The aptamer can comprise a nucleic acid, such as those found in SEQ ID NO: 1 or SEQ ID NO: 4 or SEQ ID NO: 5 or SEQ ID NO: 6, for example. The conjugates that can be used with this method are described herein.

The conjugates disclosed herein can be used to treat, alleviate, ameliorate, relieve, delay onset of, inhibit progression of, reduce severity of, and/or reduce incidence of one or more symptoms or features of a disease, disorder, and/or condition. For example, the conjugates can be used to treat cancer. Cancer types include, but are not limited to carcinoma, including that of the bladder, breast, colon, kidney, liver, lung, ovary, pancreas, stomach, cervix, thyroid and skin; including squamous cell carcinoma; tumors of mesenchymal origin, including fibrosarcoma and rhabdomyosarcoma; other tumors, including melanoma, seminoma, teratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoctanthoma, seminoma, thyroid follicular cancer and teratocarcinoma.

Specifically, the cancer can be associated with CD117 cells. For example, the cancer can be hematopoietic tumors of lymphoid lineage, including leukemia, non-Hodgkin's lymphoma, acute lymphocytic leukemia, acute lymphoblastic leukemia, B-cell lymphoma, T-cell lymphoma, Burkitt's lymphoma, Hodgkin's lymphoma, hairy cell leukemia, multiple myeloma, chronic lymphocytic leukemia; hematopoietic tumors of myeloid lineage, including acute and chronic myeloid leukemias and promyelocytic leukemia.

The treatment of cancer can comprise administering a therapeutically effective amount of the conjugate to a subject in need thereof, in such amounts and for such time as is necessary to achieve the desired result. In certain embodiments of the present invention a "therapeutically effective amount" of the conjugate is that amount effective for treating, alleviating, ameliorating, relieving, delaying onset of, inhibiting progression of, reducing severity of, and/or reducing incidence of one or more symptoms or features of cancer.

When treating cancer, the tumor size can be reduced or eliminated, or other symptoms of cancer can be reduced or eliminated.

A method for administering a conjugate to a subject suffering from cancer is provided. In some embodiments, such methods comprise administering a therapeutically effective amount of a conjugate to a subject in such amounts and for such time as is necessary to achieve the desired result (i.e. treatment of cancer). In certain embodiments of the present invention a "therapeutically effective amount" of a conjugate is that amount effective for treating, alleviating, ameliorating, relieving, delaying onset of, inhibiting progression of, reducing severity of, and/or reducing incidence of one or more symptoms or features of cancer.

Protocols for treatment can involve administering a therapeutically effective amount of a conjugate to a healthy individual (i.e. a subject who does not display any symptoms of cancer and/or who has not been diagnosed with cancer). For example, healthy individuals can be "immunized" with a conjugate prior to development of cancer and/or onset of symptoms of cancer; at risk individuals (e.g., patients who have a family history of cancer; patients carrying one or more genetic mutations associated with development of cancer; patients having a genetic polymorphism associated with development of cancer; patients infected by a virus associated with development of cancer; patients with habits and/or lifestyles associated with development of cancer; etc.) can be treated substantially contemporaneously with the onset of symptoms of cancer. Of course individuals known to have cancer may receive treatment at any time.

Disclosed herein are methods of treating cancer generally comprising targeted delivery of therapeutic agents via a conjugate comprising a nucleic acid aptamer. Such targeted delivery can be useful for delivery of one or more therapeutic agents. Alternatively or additionally, such targeted delivery can be useful for co-delivery of multiple therapeutic agents.

Methods of Diagnosis

Disclosed herein are conjugates that can be used to diagnose a disease, disorder, and/or condition (e.g., autoimmune disorders; inflammatory disorders; infectious diseases; neurological disorders; cardiovascular disorders; proliferative disorders; respiratory disorders; digestive disorders; musculoskeletal disorders; endocrine, metabolic, and nutritional disorders; urological disorders; psychological disorders; skin disorders; blood and lymphatic disorders; etc.).

Disclosed conjugates can be used to diagnose cancer. In some embodiments, such methods of diagnosis can involve the use of conjugates to physically detect and/or locate a tumor within the body of a subject.

Specifically, the nucleic acid aptamers disclosed herein can be conjugated to one or more diagnostic agents. A method for the diagnosis of cancer is provided herein. The diagnosis of cancer comprises administering a therapeutically effective amount of a conjugate as described herein to a subject, in such amounts and for such time as is necessary to achieve the desired result. In certain embodiments, a "therapeutically effective amount" of a conjugate is that amount effective for diagnosing cancer.

Disclosed herein are compositions that comprise agents which have intrinsically detectable properties. In one example, disclosed are agents which do not have intrinsically detectable properties but are associated with a substance which is detectable. Such agents are capable of simultaneously diagnosing and treating cancer. In particular, such agents are capable of treating cancer by delivery of the agent, and such conjugates are capable of diagnosing cancer by delivery of a detectable agent to the site of a tumor.

The agent used for detection can comprise a bulk material that is not intrinsically detectable. The agent can comprise one or more fluorescent, luminescent, or magnetic moieties. For example, the agent may comprise fluorescent or luminescent substances or smaller particles of a magnetic material. In some embodiments, an optically detectable moiety such as a fluorescent or luminescent dye, etc., is entrapped, embedded, or encapsulated by a particle core and/or coating layer. Fluorescent and luminescent moieties include a variety of different organic or inorganic small molecules, as described in further detail herein.

Fluorescence or luminescence can be detected using any approach known in the art including, but not limited to, spectrometry, fluorescence microscopy, flow cytometry, etc. Spectrofluorometers and microplate readers are typically used to measure average properties of a sample while fluorescence microscopes resolve fluorescence as a function of spatial coordinates in two or three dimensions for microscopic objects (e.g., less than approximately 0.1 mm diameter). Microscope-based systems are thus suitable for detecting and optionally quantitating particles inside individual cells.

Flow cytometry measures properties such as light scattering and/or fluorescence on individual cells in a flowing stream, allowing subpopulations within a sample to be identified, analyzed, and optionally quantitated (see, e.g., Mattheakis et ah, 2004, Analytical Biochemistry, 327:200). Multiparameter flow cytometers are available. Laser scanning cytometery can be used (Kamentsky, 2001, Methods Cell Biol., 63:51). Laser scanning cytometry can provide equivalent data to a flow cytometer but is typically applied to cells on a solid support such as a slide. It allows light scatter and fluorescence measurements and records the position of each measurement. Cells of interest may be relocated, visualized, stained, analyzed, and/or photographed. Laser scanning cytometers are available, e.g., from CompuCyte (Cambridge, Mass.).

An imaging system comprising an epifluorescence microscope equipped with a laser (e.g., a 488 nm argon laser) for excitation and appropriate emission filter(s) can be used. The filters can allow discrimination between different populations of particles used in the particular assay. For example, in one embodiment, the microscope is equipped with fifteen 10 nm bandpass filters spaced to cover portion of the spectrum between 520 and 660 nm, which would allow the detection of a wide variety of different fluorescent particles. Fluorescence spectra can be obtained from populations of particles using a standard UV/visible spectrometer.

Detection agents can have detectable optical and/or magnetic properties, though agents that may be detected by other approaches can be used. An optically detectable agent is one that can be detected within a living cell using optical means compatible with cell viability. Optical detection is accomplished by detecting the scattering, emission, and/or absorption of light that falls within the optical region of the spectrum, i.e., that portion of the spectrum extending from approximately 180 nm to several microns. Optionally a sample containing cells is exposed to a source of electromagnetic energy. Absorption of electromagnetic energy (e.g., light of a given wavelength) by the particle or a component thereof can be followed by the emission of light at longer wavelengths, and the emitted light is detected. In some embodiments, scattering of light by the particles is detected. For example, light falling within the visible portion of the electromagnetic spectrum, i.e., the portion of the spectrum that is detectable by the human eye (approximately 400 nm to approximately 700 nm) can be detected. In some embodiments of the invention, light that falls within the infrared or ultraviolet region of the spectrum is detected.

An optical property can be a feature of an absorption, emission, or scattering spectrum or a change in a feature of an absorption, emission, or scattering spectrum. An optical property can be a visually detectable feature such as, for example, color, apparent size, or visibility (i.e. simply whether or not the particle is visible under particular conditions). Features of a spectrum include, for example, peak wavelength or frequency (wavelength or frequency at which maximum emission, scattering intensity, extinction, absorption, etc. occurs), peak magnitude (e.g., peak emission value, peak scattering intensity, peak absorbance value, etc.), peak width at half height, or metrics derived from any of the foregoing such as ratio of peak magnitude to peak width. Certain spectra may contain multiple peaks, of which one is typically the major peak and has significantly greater intensity than the others. Each spectral peak has associated features. Typically, for any particular spectrum, spectral features such as peak wavelength or frequency, peak magnitude, peak width at half height, etc., are determined with reference to the major peak. The features of each peak, number of peaks, separation between peaks, etc., can be considered to be features of the spectrum as a whole. The foregoing features can be measured as a function of the direction of polarization of light illuminating the particles; thus polarization dependence can be measured. Features associated with hyper-Rayleigh scattering can be measured. Fluorescence detection can include detection of fluorescence modes and any of the methods described herein.

Intrinsically fluorescent or luminescent particles, particles that comprise fluorescent or luminescent moieties, plasmon resonant particles, and magnetic particles are among the detectable agents that can be used with the methods disclosed herein. Such agents can have a variety of different shapes including spheres, oblate spheroids, cylinders, shells, cubes, pyramids, rods (e.g., cylinders or elongated structures having a square or rectangular cross-section), tetrapods (particles having four leg-like appendages), triangles, prisms, etc. In general, the particles should have dimensions small enough to allow their uptake by eukaryotic cells. Typically the particles have a longest straight dimension (e.g., diameter) of 200 nm or less. In some embodiments, the particles have a diameter of 100 nm or less. Smaller particles, e.g., having diameters of 50 nm or less, e.g., 5-30 nm, can be used. T The term "particle" encompasses atomic clusters, which have a typical diameter of 1 nm or less and generally contain from several (e.g., 3-4) up to several hundred atoms.

The agents for detection can be quantum dots (QDs). QDs are bright, fluorescent nanocrystals with physical dimensions small enough such that the effect of quantum confinement gives rise to unique optical and electronic properties. Semiconductor QDs are often composed of atoms from groups II-VI or III-V in the periodic table, but other compositions are possible (see, e.g., Zheng et al, 2004, Phys. Rev. Lett., 93:7, describing gold QDs). By varying their size and composition, the emission wavelength can be tuned (i.e., adjusted in a predictable and controllable manner) from the blue to the near infrared. QDs generally have a broad absorption spectrum and a narrow emission spectrum. Thus different QDs having distinguishable optical properties (e.g., peak emission wavelength) can be excited using a single source. QDs are brighter than most conventional fluorescent dyes by approximately 10-fold (Wu et al, 2003, Nat. Biotechnol., 21:41; and Gao et al, 2004, Nat. Biotechnol, 22:969) and have been significantly easier to detect than GFP among background autofluorescence in vivo (Gao et al, 2004, Nat. Biotechnol, 22:969). Furthermore, QDs are less susceptible to photobleaching, fluorescing more than 20 times longer than conventional fluorescent dyes under continuous mercury lamp exposure (Derfus et al, 2004, Advanced Materials, 16:961).

Optically detectable agents can be metal particles. Metals of use include, but are not limited to, gold, silver, iron, cobalt, zinc, cadmium, nickel, gadolinium, chromium, copper, manganese, palladium, tin, and alloys thereof. Oxides of any of these metals can be used. Noble metals (e.g., gold, silver, copper, platinum, palladium) are preferred for plasmon resonant particles, which are discussed in further detail below. For example, gold, silver, or an alloy comprising gold, silver, and optionally one or more other metals can be used. Core/shell particles (e.g., having a silver core with an outer shell of gold, or vice versa) can be used. Particles containing a metal core and a nonmetallic inorganic or organic outer shell, or vice versa, can be used. The nonmetallic core or shell can comprise a dielectric material such as silica. Composite agents in which a plurality of metal particles are embedded or trapped in a nonmetal (e.g., a polymer or a silica shell) may be used. Hollow metal particles (e.g., hollow nanoshells) having an interior space or cavity are used in some embodiments. In some embodiments, a nanoshell comprising two or more concentric hollow spheres is used. Such a particle optionally comprises a core, e.g., made of a dielectric material.

Magnetic particles, or agents, can also be used with the conjugates as disclosed herein for detection. "Magnetic particles" refers to magnetically responsive particles that contain one or more metals or oxides or hydroxides thereof. Such particles typically react to magnetic force resulting from a magnetic field. The field can attract or repel the particle towards or away from the source of the magnetic field, respectively, optionally causing acceleration or movement in a desired direction in space. A magnetically detectable particle is a magnetic particle that can be detected within a living cell as a consequence of its magnetic properties. Magnetic particles may comprise one or more ferrimagnetic, ferromagnetic, paramagnetic, and/or superparamagnetic materials. Useful particles may be made entirely or in part of one or more materials selected from the group consisting of: iron, cobalt, nickel, niobium, magnetic iron oxides, hydroxides such as maghemite ($Y$—$Fe_2Os$), magnetite (FeSO$_4$), feroxyhyte (FeO(OH)), double oxides or hydroxides of two- or three-valent iron with two- or three-valent other metal ions such as those from the first row of transition metals such as Co(II), Mn(II), Cu(II), Ni(II), Cr(III), Gd(III), Dy(III), Sm(III), mixtures of the aforementioned oxides or hydroxides, and mixtures of any of the foregoing. Additional materials that may be used in magnetic particles include yttrium, europium, and vanadium.

Methods of Making Conjugates

The conjugates disclosed herein can comprise a nucleic acid aptamer, and an agent, such as a therapeutic or diagnostic agent. The agent can be chemically associated with the nucleic acid aptamer, for example, or can be conjugated any other way known in the art. Conjugates are typically formed by incubating the chemically modified therapeutic or diagnostic agent with the nucleic acid aptamer.

Conjugates as disclosed herein can be manufactured using any available method. When associating aptamers with agents, it is desirable to have an agent which can be efficiently linked to a negatively charged nucleic acid aptamer using simple chemistry without adversely affecting the 3-dimensional characteristic and conformation of the nucleic acid aptamer. It is desirable that the conjugate should be able to avoid uptake by the mononuclear phagocytic system after systemic administration so that it is able to reach specific organs, tissues, and/or cells in the body.

The nucleic acid aptamer can be associated with a second therapeutic or diagnostic agent to be delivered. In some embodiments, therapeutic or diagnostic agents are not covalently associated with the aptamer. To give another example, agents may comprise polymers, and therapeutic or diagnostic agents may be associated with the surface of, encapsulated within, and/or distributed throughout the aptamer. Agents are released by diffusion, degradation of the aptamer, and/or combination thereof. In some embodiments, polymers degrade by bulk erosion. In some embodiments, polymers degrade by surface erosion. In some embodiments, therapeutic or diagnostic agents are covalently associated with an aptamer. For such conjugates, release and delivery of the therapeutic or diagnostic agent to a target site occurs by disrupting the association. For example, if an aptamer is associated with an agent by a cleavable linker, the agent is released and delivered to the target site upon cleavage of the linker.

The conjugates can be physically associated with the nucleic acid aptamer. In some embodiments, physical association may be covalent. For example, the aptamer and agent may be directly associated with one another, e.g., by one or more covalent bonds, or may be associated by means of one or more linkers. In some embodiments, the linker forms one or more covalent or non-covalent bonds with the complex and one or more covalent or non-covalent bonds with the aptamer, thereby attaching them to one another.

Any suitable linker can be used in accordance with the present invention. Linkers may be used to form amide linkages, ester linkages, disulfide linkages, etc. Linkers may contain carbon atoms or heteroatoms (e.g., nitrogen, oxygen, sulfur, etc.). Typically, linkers are 1 to 50 atoms long, 1 to 40 atoms long, 1 to 25 atoms long, 1 to 20 atoms long, 1 to 15 atoms long, 1 to 10 atoms long, or 1 to 10 atoms long. Linkers may be substituted with various substituents including, but not limited to, hydrogen atoms, alkyl, alkenyl, alkynl, amino, alkylamino, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, and ureido groups. As would be appreciated by one of skill in this art, each of these groups may in turn be substituted.

A linker can be an aliphatic or heteroaliphatic linker. For example, the linker can a polyalkyl linker. The linker can be a polyether linker. The linker can be a polyethylene linker, such as PEG. The linker can be a short peptide chain, e.g., between 1 and 10 amino acids in length, e.g., 1, 2, 3, 4, or 5 amino acids in length, a nucleic acid, an alkyl chain, etc.

The linker can be a cleavable linker. To give but a few examples, cleavable linkers include protease cleavable peptide linkers, nuclease sensitive nucleic acid linkers, lipase sensitive lipid linkers, glycosidase sensitive carbohydrate linkers, pH sensitive linkers, hypoxia sensitive linkers, photo-cleavable linkers, heat-labile linkers, enzyme cleavable linkers (e.g. esterase cleavable linker), ultrasound-sensitive linkers, x-ray cleavable linkers, etc. In some embodiments, the linker is not a cleavable linker.

Any of a variety of methods can be used to associate a linker with an aptamer and agent. General strategies include passive adsorption (e.g., via electrostatic interactions), multivalent chelation, high affinity non-covalent binding between members of a specific binding pair, covalent bond formation, etc. (Gao et al, 2005, Curr. Op. Biotechnol., 16:63). Click chemistry can be used to associate a linker with an agent (e.g. Diels-Alder reaction, Huigsen 1,3-dipolar cycloaddition, nucleophilic substitution, carbonyl chemistry, epoxidation, dihydroxylation, etc.).

A bifunctional cross-linking reagent can be employed. Such reagents contain two reactive groups, thereby providing a means of covalently associating two target groups. The reactive groups in a chemical cross-linking reagent typically belong to various classes of functional groups such as succinimidyl esters, maleimides, and pyridyldisulfides. Exemplary cross-linking agents include, e.g., carbodiimides, N-hydroxysuccinimidyl-4-azidosalicylic acid (NHS-ASA), dimethyl pimelimidate dihydrochloride (DMP), dimethylsuberimidate (DMS), 3,3'-dithiobispropionimidate (DTBP), N-Succinimidyl 3-[2-pyridyldithio]-propionamido (SPDP), succimidyl α-methylbutanoate, biotinamidohexanoyl-6-amino-hexanoic acid N-hydroxy-succinimide ester (SMCC), succinimidyl-[(N-maleimidopropionamido)-dodecaethyleneglycol] ester (NHS-PEO 12), etc. For example, carbodiimide-mediated amide formation and active ester maleimide-mediated amine and sulfhydryl coupling are widely used approaches.

Common schemes for forming a conjugate involve the coupling of an amine group on one molecule to a thiol group on a second molecule, sometimes by a two- or three-step reaction sequence. A thiol-containing molecule may be reacted with an amine-containing molecule using a heterobifunctional cross-linking reagent, e.g., a reagent containing both a succinimidyl ester and either a maleimide, a pyridyldisulfide, or an iodoacetamide. Amine-carboxylic acid and thiol-carboxylic acid cross-linking, maleimide-sulfhydryl coupling chemistries (e.g., the maleimidobenzoyl-N-hydroxysuccinimide ester (MBS) method), etc., may be used. Polypeptides can conveniently be attached to particles via amine or thiol groups in lysine or cysteine side chains respectively, or by an N-terminal amino group. Nucleic acids such as RNAs can be synthesized with a terminal amino group. A variety of coupling reagents (e.g., succinimidyl 3-(2-pyridyldithio)propionate (SPDP) and sulfosuccinimidyl-4-(N-maleimidomethyl)cyclohexane-1-carboxylate (sulfo-SMCC) may be used to associate the various components of conjugates. Agents can be prepared with functional groups, e.g., amine or carboxyl groups, available at the surface to facilitate association with a biomolecule. Any biomolecule can be attached to another molecule described herein using any of the methods described herein.

Exemplary non-covalent interactions include, but are not limited to, charge interactions, affinity interactions, metal coordination, physical adsorption, host-guest interactions, hydrophobic interactions, FI stacking interactions, hydrogen bonding interactions, van der Waals interactions, magnetic interactions, electrostatic interactions, dipole-dipole interactions, etc.

A nucleic acid aptamer can be associated with an agent via charge interactions. For example, an agent may have a cationic surface or may be reacted with a cationic polymer, such as poly(lysine) or poly(ethylene imine), to provide a cationic surface. The agent surface can then bind via charge interactions with a negatively charged complex. One end of the nucleic acid aptamer is, typically, attached to a negatively charged polymer (e.g., a poly(carboxylic acid)) or an additional oligonucleotide sequence that can interact with the cationic polymer surface without disrupting the binding affinity of the nucleic acid aptamer for its target.

An agent can be associated with a nucleic acid aptamer via hydrogen bonding interactions. For example, an oligonucleotide having a particular sequence may be attached to the surface of the agent, and an essentially complementary sequence may be attached to one or both ends of the complex such that it does not disrupt the binding affinity of the nucleic acid aptamer for its target. The nucleic acid aptamer will then bind to the agent via complementary base pairing with the oligonucleotide attached to the agent. Two oligonucleotides are essentially complimentary if about 80% of the nucleic acid bases on one oligonucleotide form hydrogen bonds via an oligonucleotide base pairing system, such as Watson-Crick base pairing, reverse Watson-Crick base pairing, Hoogsten base pairing, etc., with a base on the second oligonucleotide. Typically, it is desirable for an oligonucleotide sequence attached to the agent to form at least about 6 complementary base pairs with a complementary oligonucleotide attached to the nucleic acid aptamer.

Kits

Disclosed herein are kits comprising a conjugate, wherein the conjugate comprises a nucleic acid aptamer and an agent. For example, the invention provides a kit comprising the conjugate and instructions for use. A kit may comprise multiple different conjugates. A kit may comprise any of a number of additional components or reagents in any combination (e.g. pharmaceutically acceptable excipients). All of the various combinations are not set forth explicitly but each combination is included in the scope of the invention.

A kit may include, for example, (i) a complex comprising a nucleic acid aptamer and one or more therapeutic or diagnostic agents to be delivered; (ii) instructions for administering the conjugate to a subject in need thereof.

Kits typically include instructions for use of conjugates. Instructions may, for example, comprise protocols and/or describe conditions for production of complexes or targeted conjugates, administration of conjugates to a subject in need thereof, design of conjugates, etc. Kits will generally include one or more vessels or containers so that some or all of the individual components and reagents may be separately housed. Kits may also include a means for enclosing individual containers in relatively close confinement for commercial sale, e.g., a plastic box, in which instructions, packaging materials such as Styrofoam, etc., may be enclosed. An identifier, e.g., a bar code, radio frequency identification (ID) tag, etc., may be present in or on the kit or in or one or more of the vessels or containers included in the kit. An identifier can be used, e.g., to uniquely identify the kit for purposes of quality control, inventory control, tracking, movement between workstations, etc.

A number of embodiments of the invention have been described. Nevertheless, it will be understood that various modifications may be made without departing from the spirit and scope of the invention. Accordingly, other embodiments are within the scope of the following claims.

Examples

The CD117 receptor-expressing cell line HEL (ATCC, Manassas, Va.), was used to select single stranded (ss) DNA aptamers with high affinity for CD117-positive cells. CD117 recombinant protein with a polyhistidine (His) tag at the C-terminus (Sino Biological Inc. Beijing, China) was used to further select DNA specific for the CD117 receptor at the protein level. The CD117-negative cell lines tested were: B lymphoma cell lines CA46 (ATCC, Manassas, Va.); breast cancer cell lines 468 (kindly provided by Dr. Haifa Shen, Houston Methodist Hospital) and prostate cancer cell lines LNCaP (ATCC, Manassas, Va.). All suspension cells were cultured with RPMI1640 medium (Fisher Scientific, Pittsburgh, Pa.) with 10% FBS (Atlanta Biologicals, Lawrenceville, Ga.). All adhesion cell lines were cultured with DMEM (Atlanta Biologicals, Lawrenceville, Ga.) with 10% FBS.

Hybrid Systematic Evolution of Ligands by Exponential Enrichment (SELEX)

The DNA library used for aptamer selection consisted of a central, continuous stretch of 35 randomized sequences flanked by PCR primer sequences (5'-GAGGCATACCA-GCTTATTCAA-35N-ATAGTAAGTGC AATCTGCGAA 3'. Cy3-labeled 5' primer (5'-cy3-GAGGCATACCAGCTT-ATTCAA 3', SEQ ID NO: 2) and biotinylated 3' primer (5'-biotin-TTCGCAGATTGCACTTACTAT 3', SEQ ID NO: 3) were used in the initial PCR. DNA library and primers were purchased from Integrated DNA Technologies (Coralville, Iowa). The synthesized DNA library was purified by reversed-phase ion pairing high-performance liquid chromatography (HPLC, Integrated DNA Technologies).

The whole aptamer developing process was performed as previously reported (Zhang Y, Chen Y, Han D, Ocsoy I, Tan W: Aptamers selected by cell-SELEX for application in cancer studies. Bioanalysis 2010, 2(5):907-918). Briefly, aptamers selection was begun with CD117 positive cell line HEL After 10 rounds positive cell selection, the enriched DNA pool was used in sequential protein-based selection by incubation with CD117 recombinant protein (Sino Biological Inc. Beijing, China). The protein selection process was repeated three times. After a total of 13 rounds of cell and protein-based selection, binding affinity and specificity of the selected pool was determined by flow cytometry (LSRII, BD Biosciences, San Jose, Calif.). The final selected pool was sequenced using second-generation sequencing (LC Sciences, Houston, Tex.).

First, ssDNA library was incubated with 5-10×10$^6$ CD117-positive HEL Acute myeloid leukemia cells for 30 min at room temperature. Following a wash with DPBS buffer (Fisher scientific) supplemented with 0.1% BSA, 0.1 g/L tRNA, and 5 mM $MgCl_2$, bound DNA was eluted by heating the mixture to 95° C. for 10 min. The eluted sequences were PCR-amplified using the Cy5-labeled or non-fluorescent labeled forward and biotin-labeled reverse primers and the following cycle settings: denaturation at 94° C. for 30 s, annealing at 58° C. for 30 s, and extension at 72° C. for 30 s. The number of PCR cycles was optimized as below for each round of selection and ranged from 10 to 30: PCR products were separated on 2% agarose gels (Bio-Rad, Hercules, Calif.), and the highest cycle that displayed absence of nonspecific bands was chosen as the cycle number for subsequent amplification steps. Following amplification, ssDNA sequences were separated from the biotinylated antisense ssDNA by alkaline denaturation using 200 mM NaOH, and then affinity purified with streptavidin-coated sepharose beads (Fisher Scientific). The separated ssDNA solution was passed through a desalting Nap-5 column (Fisher Scientific) to remove NaOH, and the purified ssDNA was used for the next round of selection. Combined, this cell line-based selection was repeatedly conducted for total ten times.

In the second step, the aptamer was continued to be selected by a recombinant CD117 protein (Sino Biological, Beijing, China). Ni-NTA magnetic beads (Qiagen, Valencia, Calif.) were pre-blocked with 5% bovine serum albumin (BSA, Fisher Scientific), washed with DPBS buffer, incubated with recombinant His tag-CD117 protein for 30 min, and washed again with DPBS buffer. Then, the CD117 protein-coated beads were incubated with the enriched DNA pool for 30 min, centrifuged for 5 min at 800 rpm, and washed twice. The eluted DNA then underwent two additional rounds of the recombinant protein-based selection.

Cell Binding Assay

Flow cytometry was used to monitor the enrichment of ssDNA pools during the selection and to determine the binding affinity and specificity of the synthesized aptamers in each ssDNA pool. The Cy3-labeled ssDNA pool or individual isolated aptamers were incubated for 30 min at room temperature (RT) with $1 \times 10^5$ target or control cells at the indicated concentrations. The cells were washed once with 500 μl of PBS and re-suspended in 500 μl of PBS. The fluorescence intensity was determined with a FACScan cytometer (LSRII, BD Biosciences, San Jose, Calif.) by counting 10,000 events. The Cy3-labeled initial ssDNA library was used as a background control.

Thioflavin T Staining for Determining G4 Structure of the CD117 Aptamer

To detect G4 structure, the CD117 aptamer No. 9 was stained by Thioflavin T (Th-T) as the reference reported (Renaud de la Faverie A, Guedin A, Bedrat A, Yatsunyk L A, Mergny J L: Thiflavin T as a fluorescence light-up probe for G4 formation. Nucleic acids research 2014, 42(8):e65). Briefly, oligonucleotides and Thioflavin T (Sigma Aldrich, St. Louis, Mo.) were mixed at 1 and 0.5 uM final concentrations, respectively, and cultured for 30 minutes at room temperature. Fluorescence emission was collected at 490 nm after excitation at 425 nm in microplate reader (Biotek, Winooski, Vt.). Control aptamer #6: CD4 DNA aptamer (Zhao N, Pei S N, Parekh P, Salazar E, Zu Y: Blocking interaction of viral gp120 and CD4-expressing T cells by single-stranded DNA aptamers. The international journal of biochemistry & cell biology 2014, 51:10-18) and control aptamer #2: CD30 aptamer (Parekh P, Kamble S, Zhao N, Zeng Z, Portier B P, Zu Y: Immunotherapy of CD30-expressing lymphoma using a highly stable ssDNA aptamer. Biomaterials 2013, 34(35):8909-8917), which don't have GGG or GGGG repeat, were considered as negative controls.

Cell Staining Analysis of CD117 Aptamer by Fluorescent Microscopy

Specific cell binding of aptamer was further examined using fluorescence microscopy. In this experiment, CD117-negative U937 cells ($1 \times 10^5$) were used as a control and pre-stained with 25 nM of carboxyfluorescein diacetate succinimidyl ester (CF SE, invitrogen, Eugene, Oreg., USA) in 1 ml of PBS in the dark at room temperature for 10 minutes. The cells were then to stop labeling with pre-warmed 100% FBS, and washed with 1 ml 2% FBS/PBS third times and re-cultured in 4 ml fresh RPMI 1640 medium containing 10% FBS for 30 minutes before use. Subsequently, a cell mixture was prepared by mixing the CFSE-labeled U937 cells ($5 \times 10^5$) with equal number of fresh HEL cells in RPMI buffer at 1:1 ratio. Cy3-labeled CD117 aptamer probe (50 nM) was added to the cell mixture and incubated at room temperature for 30 minutes. After washing, slides of cell smears were prepared and examined under a fluorescent miscroscope (Olympus FluoView™ 1000, Olympus America, Center Valley, Pa.).

CD117 Aptamer Conjugated with Methotrexate

Mexthotrexate was activated by linking with NHS. 15 mg (33 μmol) of Methotrexate was dissolved in 500 μl of DMF (Dimethylformamide) and 100 μl of NMM (N-Methylmorpholine), then 11 mg (36 μmol) of TSTU (O—(N-Succinimidyl)-1,1,3,3-tetramethyl uranium tetrafluoroborate) was added and stirred for 15 min at RT, then 5 mg (43.5 μmol) of NHS was added and stirred at RT overnight. Then, activated Mexthothrexate was reacted with amino-modified CD117 aptamer. Amino-linked oligonucleotide of 5AmMC6-CD117 (3.0 mg, 0.12 μmol) was dissolved in 500 μl of deionized water in a 2 ml of plastic microtube, following add 200 μL of fresh prepared Methotrexate hydroxysuccinimide ester reaction solution. After 1 h, 200 μl of the active ester reaction solution was added again. 400 μl (22 μmol) of Methotrexate hydroxysuccinimide ester was added. The reaction solution was stirred overnight at RT, and then purified by HPLC on reverse phase chromatography. Mobile phase A was 100 mM triethylamine acetate aqueous solution. Mobile phase B was acetonitrile containing 5% of 100 mM triethylamine acetate aqueous solution. The gradient was 100% A for 5 min, 100% A to 85% B for 41 min, 85% B for 3 min, 85% B to 0% B for 3 min, 0% B 3 min at a flow rate of 1 ml min$^{-1}$. Eluent at 13.5 min was collected. The purification was repeated again to completely remove free Methotrexate and dried by lyophilisation to give 1.2 mg of CD117 coupling Methotrexate as pale white solid.

Cellular CD117 Protein Precipitation by CD117 Aptamer and Detection by Western Blotting $5 \times 10^6$ HEL and U937 cells were collected and lysated by the whole protein lysis buffer (Thermo Fisher Scientific, Rockford, Ill.) for 30 minutes on ice, and followed by centrifuge at 10,000 rpm. The supernatants were cultured with biotin-labeled CD117 aptamer (100 nM), control CD4 aptamer (100 nM), and CD30 aptamer (100 nM), and bead alone for 30 minutes at room temperature. Post 500 μl PBS washing, 100 μl of streptavidin beads were added (Fisher scientific, Rockford, Ill.), and the solution was incubated for another 30 minutes. After PBS buffer washing, 100 μl 1× loading buffer was added, and the solution was boiled for 5 minutes. Supernatants were collected and proteins were separated in SDS-PAGE gel, subsequently transferred onto PVDF membranes (Thermo Fisher Scientific, Rockford, Ill.) and detected by anti-CD117 antibody (Cell signaling technology, Danvers, Mass.).

Mass Spectrometry Analysis

The precipitated cellular proteins by the CD117 aptamer, CD4 aptamer or bead alone were separated by SDS-PAGE gel, and stained by silver stain kit (Thermo Fisher Scientific, Rockford, Ill.). The stained bands of precipitated cellular proteins were cut and their identifications were determined by mass spectrometry analysis.

Cell Growth Inhibition and Apoptosis Detection

Cell growth inhibition was monitored by MTT (MTT (3-[4,5-dimethylthiazol-2-yl]-2,5-diphenyltetrazolium bromide) assay post treatment. Cells (5000) were treated by CD117 Apt-MTX or equal molar free MTX in RPMI 1640 medium for 2 h. After replacement with fresh medium containing 10% serum, cells were cultured for an additional 48 hours and then 10 µl of MTT solution (5 mg/mL in PBS) were added to each well. After a further 4 h of incubation, the culture medium was removed and the formazan crystals in the cells were solubilized with 100 µl of DMSO for 15 minutes. The UV absorbance at 570 nm was measured with a microplate reader.

Treated cells also were investigated by apoptosis assay. Annexin V-APC staining (BD Biosciences, San Jose, Calif.) was performed according to the manufacturer's instructions. The cell samples were analyzed using a FACS caliber (BD Biociences, San Jose, Calif., USA) flow cytometry equipped with cellquest software.

Cell Cycle Analysis

The treated cells by Apt-MTX, equal molar free MTX, or Apt alone, and non-treated cells ($1 \times 10^6$) were collected by centrifuge at 1000 rpm for 5 minutes, washed by cold PBS buffer without $Mg^{2+}$, and fixed in 70% ethanol at $-20°$ C. for at least 2 hours. Then, incubated with Propidium Iodide (PI)/Triton X-100 staining solution: 0.1% Triton X-100, 20 µg/ml PI, 0.2 mg/ml DNAse-free RNAse A (Sigma Aldrich, St. Louis, Mo.) for 30 minutes at room temperature. Post washing by cold PBS buffer, cells were suspended by 500 µl cold PBS buffer, and analyzed using a FACS caliber (BD Biosciences, San Jose, Calif., USA) flow cytometry equipped with cellquest software.

Selective Cell Inhibition Assays by Flow Cytometry

The CD117 Apt-MTX, equal molar free drug MTX or aptamer alone was added into a cell mixture that contained CD117-expressing HEL and CD117-negative U937 cells at an initial ratio of 1:1 (total $1 \times 10^5$ cells). After 2 h of treatment, the mixed cells were seeded in fresh RPMI 1640 medium containing 10% serum and continuously cultured for 48 h. Cells were then harvested and stained by PE-conjugated anti-CD15 antibody (BD Biosciences, San Jose, Calif.). As CD15 expressed in U937 and not in HEL cells, the mixed cells were separated by flow cytometry based on their CD15 expression, and each cell population was counted separately.

Results

Development of CD117-Specific and AML Cell-Targeting ssDNA Aptamers

To develop CD117-specific and AML cell-targeting aptamers, a ssDNA library was synthesized as described under materials and methods and a hybrid SELEX was conducted (FIG. 1A). After 10 rounds of AML cell-based selection (HEL cell line) and 3 rounds of recombinant CD117 protein-based enrichment, a final ssDNA pool was sequenced. Second generation sequencing identified one dominant sequence (aptamer No. 4), accounting for 82% of total 500,000 reads. Additional four small clusters of sequences, aptamers No. 1, No. 5, No. 6, No. 7 were also identified, each of them had >1% of total reads (FIG. 1B). Interestingly, aptamers No. 4, 5, and 6 have common conserved sequence of 5'-GGGGC-CGGGGCAAGGGGGGGGTAnnGTGGTAGGAC-3' (FIG. 1C). However, the aptamer No. 1 had a different sequence (FIG. 1B). The consensus sequence of aptamer GGGGC-CGGGGCAAGGGGGGGGTAnnGTGGTAGGAC is not found in SEQ ID NO: 1 (ATTGCACGGGGATCGAGCA-GGGGACCAGGTGAATG). For cell binding assay, aptamers No. 9 and No. 8 were synthesized with Cy3 fluorescence reporter at 5' end terminal of sequences and incubating with cultured AML cells (HEL) Flow cytometry revealed that both aptamers No. 9 and No. 8 were able to binding to cultured AML cells with a similar pattern (upper panel of FIG. 1C). However, further validation by using patient marrow specimens showed that aptamer No. 9 specifically targeted primary AML cells that were highlighted by anti-CD117 antibody, but aptamer No. 8 did not react to primary AML cells (lower panel of FIG. 1C).

Figure 2:
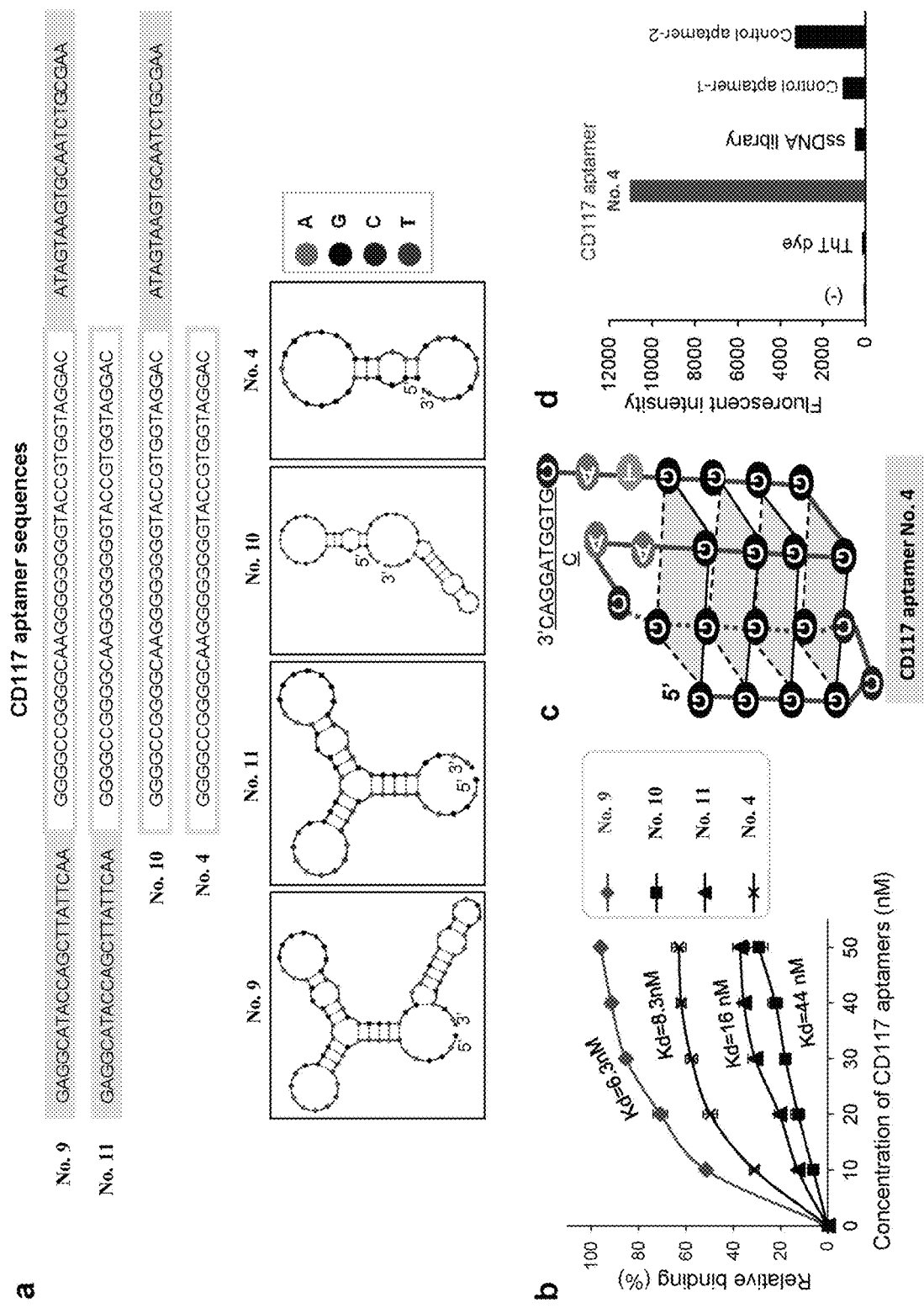
FIG. 2 shows the characterization and optimization of the CD117 aptamer No. 9. (a) the sequences of No. 4 including two primers region and sequence between primer regions, and chopped sequences derived from the No. 4, based on 2-D predicted structure by IDT software and primer regions. (b) Cell-binding ability of the four aptamers using a flow cytometry-based assay with CD117-positive cells (HEL cell line). Sequence No. 9 had highest binding ability, leading to maximum binding at 50 nM with a Kd of 6.3 nM, compared with the other three chopped aptamers. (c) Predicted 3-D G-quadruplex structure of the aptamer No. 4. (d) ThT staining confirmed that there was functional G-quadrupx in CD117 aptamer No. 4 (SEQ ID NO: 4).

To determine minimal functional sequence, three truncated forms of aptamer No. 9 were synthesized, including No. 4 with forward primer region and deletion of 3' end primer region (aptamer No. 11), with reverse primer region with deletion of 5' end primer region (aptamer No. 10), and No. 4 without primer regions (FIG. 2A). The 2-D structures of aptamer No. 9 and its truncated forms were predicted. Cell binding assay showed that aptamer No. 9 had the highest binding ability with a Kd-6.3 nM, and truncated forms showed decreased binding capacity to cultured AML cells with Kd ranging 8.3 nM to 44 nM (FIG. 2B). These findings indicated that the full length sequence No. 9 was indispensable for high affinity cell binding of CD117 aptamer. Moreover, sequence alignment analysis revealed a complete G-quadruplex structure within No. 4 sequence (FIG. 2C) and function of G-quadruplex structure was also confirmed by the ThT staining assay (FIG. 2D) (Renaud de la Faverie A, Guedin A, Bedrat A, Yatsunyk L A, Mergny J L: Thioflavin T as a fluorescence light-up probe for G4 formation. Nucleic acids research 2014, 42(8):e65). Therefore, aptamer No. 9 was used for the remaining studies.

Figure 3:
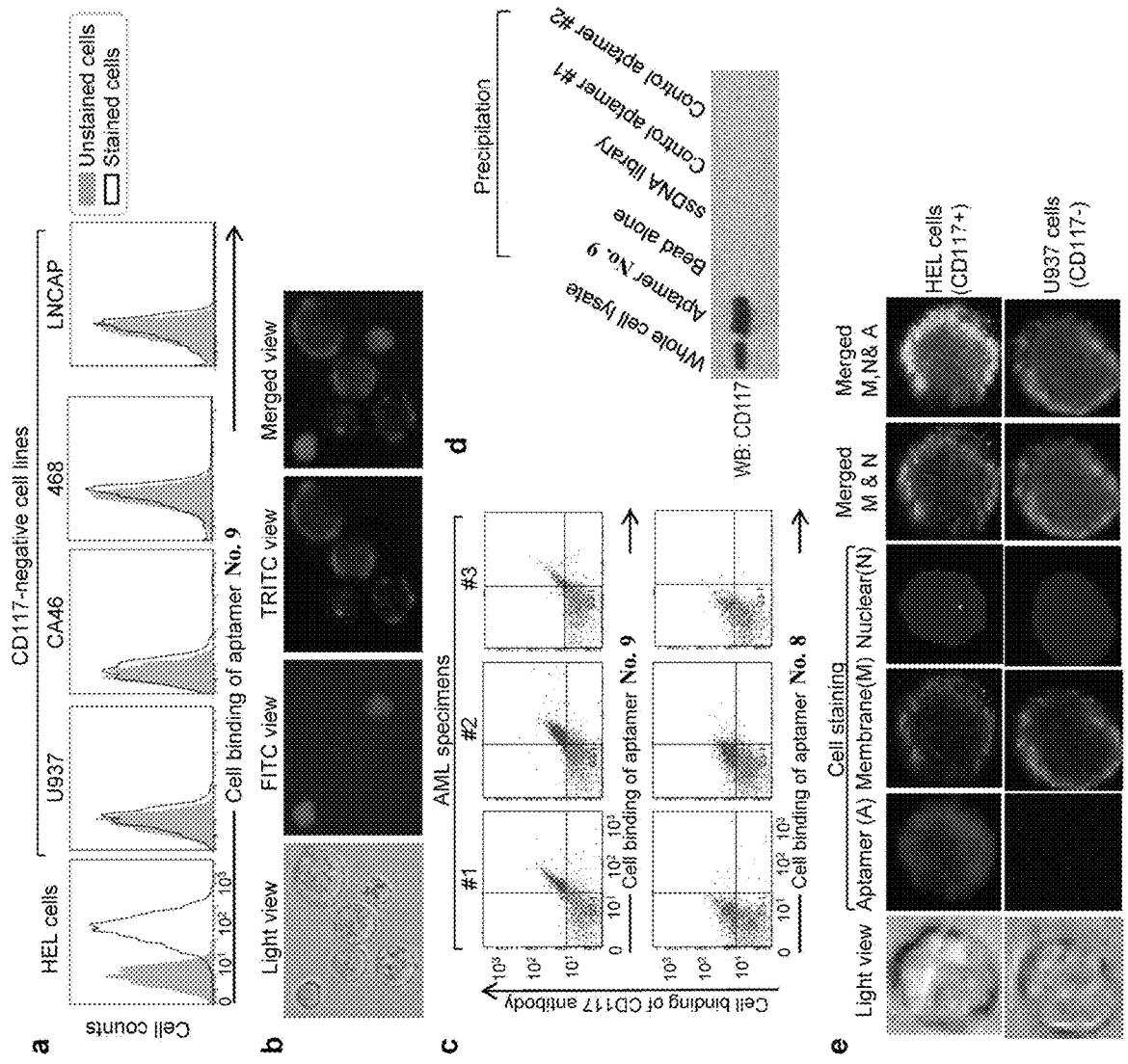
FIG. 3 shows the specificity of the synthesized CD117 aptamer No. 9. (a) CD117-positive cell line HEL and CD117-negative cell lines: B lymphoma cell line: CA46, breast cancer cell line: MDA-MB-468, T lymphoma cell line: U937, and prostate cancer cell line: LNCaP, were stained with the aptamer No. 9, and cell binding was determined by flow cytometry. (b) A cell mixture of HEL (CD117-positive) and CFCE pro-stained U937 (CD117-negative) cells were stained by Cy3 labeled aptamer 9. The resultant cell bindings were observed by fluorescent microscope. (c) Pretreated AML specimens by red blood cell lysis ACK buffer were simultaneously stained by Cy3-labeled aptamer No. 9, or No. 8, and U subsequent FITC-labeled anti-CD117 antibody. The resultant cell binding was detected by flow cytometry. (d) HEL cell lysate was precipitated by CD117 aptamer No. 9, ssDNA library or control aptamers #1: CD4 aptamer or #2: CD30 aptamer, followed to be separated on SDS-PAGE gel, and detected by western blotting with anti-CD117 antibody. (e) Cells were pro-stained by membrane dye: Alex 488 and nuclear dye: Hoechst 33342, and followed to be stained by Cy3-labeled CD117 aptamer No. 9. Stained cells were observed by confocal-fluorescent microscope.

To validate AML cell specificity, multiple CD117-negative cell lines (B-lymphoma CA46, histiocytic lymphoma U937, breast cancer 468, and prostate cancer LNCAP) were incubated with Cy3-labeled aptamer No. 9 and cell binding was detected by flow cytometry (FIG. 3A). In addition, a mixture of fresh HEL cells and pre-stained U937 cells was treated with Cy3-labeled aptamer and resultant cell binding was examined under a fluorescent microscope. In the cell mixture, the aptamer selectively stained HEL cells (red fluorescence) and did not bind to off-target U937 cells (pre-stained in green fluorescence) (FIG. 3B). Moreover, three marrow specimens of AML patients were treated with Cy3-labeled aptamers and FITC-cojugated anti-CD117 antibody simultaneously. Flow cytometry analysis indicated that the aptamer No. 9 specifically targeted the same populations of AML cells that were highlighted by anti-CD117 antibody in each marrow specimen (FIG. 3C). In contrast, the aptamer sequence No. 8 did not react to primary AML cells, although it was able to bind to cultured HEL cells.

To identify whether the aptamer recognizes cellular CD117 proteins, immunoprecipitation of HEL cell lysates was performed with the aptamer No. 9, resultant cellular proteins were separated gel electrophoresis, and probed by anti-CD117 antibody. Western blotting demonstrated that the aptamer No. 9 specifically reacted with cellular CD117 proteins and thus, raised the same band as observed in whole cell lysates (FIG. 3D). In contrast, no CD117 proteins were detected in control reactions with ssDNA library or non-relevant control aptamer sequences. The gel bands of aptamer-precipitated cellular proteins were also collected and sequenced by mass spectrometry (MS). The presence of CD117 proteins in CD117-specific aptamer-precipitated cellular products was confirmed with a protein ID: P10721, which was not detected in control reactions. These findings indicate that the developed aptamer is AML-targeted and CD117-specific.

Finally, for intracellular drug delivery, the cell surface receptor-mediated internalization approach has been widely used in antibody-drug conjugates, such as brentuximab (an anti-CD30 antibody-drug conjugate for lymphoma therapy) (Bradley A M, Devine M, DeRemer D: Brentuximab vedotin: an anti-CD30 antibody-drug conjugate. AJHP 2013, 70(7):589-597). To investigate internalization, cultured cells were membrane stained and incubated with Cy-3 labeled aptamer. Fluorescent microscopic examination revealed that the aptamer bound cell surface as early as 5 min post treatment and gradually entered into AML cells (HEL expressing CD117). However, there was no aptamer signals were detected in CD117-negative control cells (FIG. 3E).

Formulation of Aptamer-Drug Conjugates Specifically Targeting AML Cells

Figure 4:
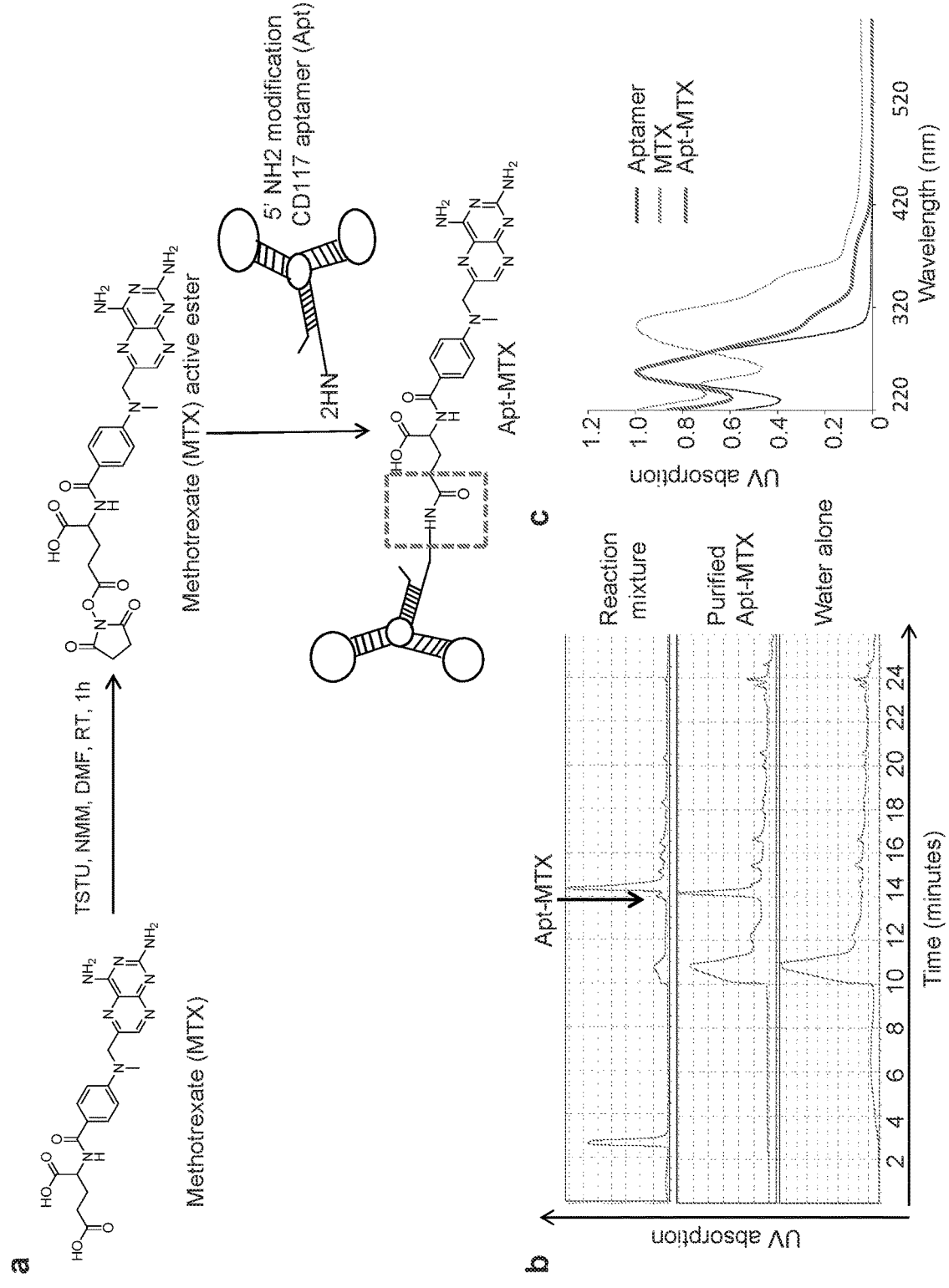
FIG. 4 shows an exemplary aptamer-drug conjugate: (a) The process of aptamer-drug conjugation. Methotrexate was activated by an NHS active ester group, following conjugation with a 5' modified NH2 group aptamer No. 9 to produce aptamer-methotrexate conjugate (Apt-MTX). (b) The identification of the purified product Apt-MTX by HPLC. (c) Detection of aptamer, MTX and Apt-MTX product by UV spectroscopy.

For targeting AML therapy, aptamer-drug conjugates were formulated by synthesizing aptamer No. 9 sequence directly to chemotherapeutic drug methorexate (MTX). First, MTX molecules were added with an active NHS group and then reacted with synthetic CD117 aptamer sequence containing a functional amino-group (FIG. 4A). Resultant products were purified by HPLC isolation and the formed aptamer-MTX conjugates (Apt-MTX) were evaluated (FIG. 4B). In addition, the presence of MTX in final Apt-MTX product was confirmed by UV detection (FIG. 4C).

Since the aptamer sequence is able to specifically bind and result in internalization through interaction CD117-mediated internalization (FIG. 3E), the formed Apt-MTX can deliver the carrying drug selectively into cells of interest, leading to AML cell death with no toxicity off-target cells (FIG. 5A). To evaluate cellular effect, AML cells (HEL) and CD117-negative control cells (U937) were treated with Apt-MTX for 2 hours and cultured in fresh medium for 48 hr. Resultant changes in cell proliferation were monitored by MTT assays. Apt-MTX treatment resulted in 80% growth inhibition of AML cells at 10 nM final concentration of MTX payload, which had little effect on control cells (FIG. 5B). While, equal molar free MTX treatment had minimal effect on both cells under the same condition and both cells showed very similar sensitivity to free MTX with about 30% inhibition at 100 nM final concentration, 10 folds of effective dose of Apt-MTX to treat AML cells. Meanwhile, cells were also stained with Annexin V and apoptotic cells were quantified by flow cytometry. The Apt-MTX treatment containing 10 nM MTX payload significantly induced HEL cell apoptosis, but had little toxicity effect on control cells (FIG. 5C). In contrast, equal molar free MTX treatment at the same dose showed minimal effect on both HEL and control cells. In addition, cell growth cycle analysis demonstrated that Apt-MTX treatment induced G1 phase arrest of more than 90% HEL cells, while showed minimal effect on CD117-negative control cells (FIG. 5D). These findings indicated that Apt-MTX was able to specifically deliver MTX into AML cells for inhibition effect even containing a sub-toxic dose, at which equal molar free MTX showed minimal cellular effect.

Apt-MTX Treatment Selectively Inhibited Primary AML Cells Present in Patient Marrow Specimens To examine target therapy potential, a cell mixture was made of HEL and U937 cells at 1:1 ratio, since both cells showed similar sensitivity to free MTX treatment (FIG. 5B). The cell mixture was treated with Apt-MTX or equal molar free MTX as described above (FIG. 6A), and cultured for 48 hr. Residual cells were then stained with anti-CD15 antibody for identification of U937 cells since HEL cells are negative. Flow cytometry analysis revealed that Apt-MTX selectively inhibited HEL cells in cell mixture, while under the same conditions, equal molar free MTX showed similar effects on both HEL cells and U937 control cells (FIG. 6B). In addition, cell mixtures stained with PI and total dead cells under each treatment condition were counted. The Apt-MTX treatment selectively triggered death of >40% mixed cells much higher than that by equal molar free MTX treatment (FIG. 6C). As showed in FIG. 6B, the detected total dead cells were HEL cells within the mixture.

Figure 7:
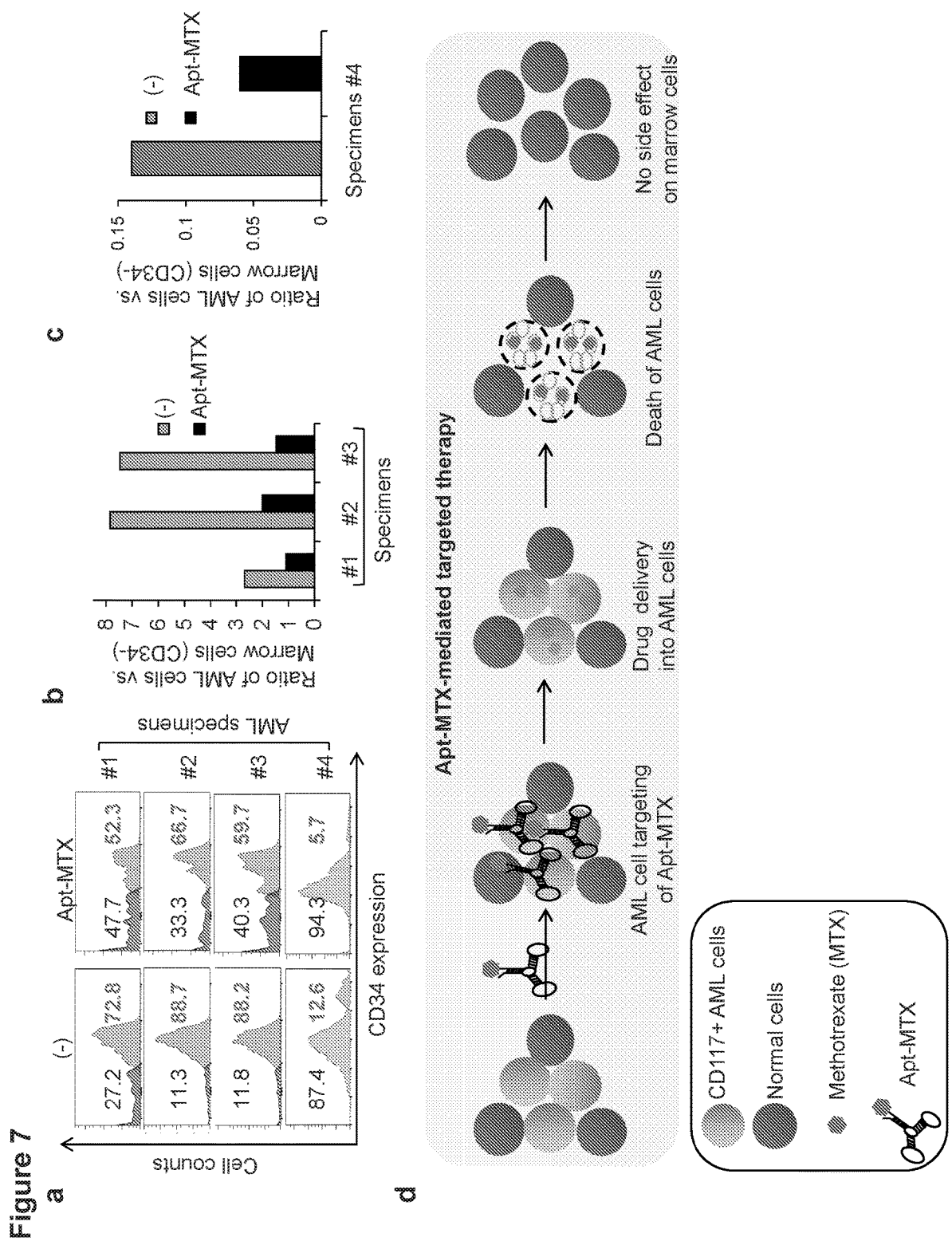
FIG. 7 shows the specific treatment of AML cells derived from AML patient specimens by Apt-MTX: (a) AML samples were pre-treated by Ammonium-Chloride-Potassium (ACK) lysis buffer to eliminate red blood cells, followed to be treated by Apt-MTX. Post 48 h treatments, changes in CD34-positive leukemia blast cells were quantified by flow cytometry. (b) and (c) Based on the above flow data, quantification of the ratio of CD34+leukemia cells and CD34-normal marrow mononuclear cells. (d) A schematic illustration displaying the CD117 aptamer development, CD117 aptamer conjugation with ant-cancer drug, and CD117 Apt-MTX mediated specific treatment to AML cells with no side toxicity to background marrow mononuclear cells.

To test therapy effect on primary leukemia cells, marrow aspirate specimens from AML patients were used. Notably, primary AML cells could be distinguished from background marrow cells by high level expression of CD117 and CD34. Patients specimens were treated with CD117-specific Apt-MTX as described above and cultured for 2 days. The treated specimens were then stained with anti-CD34 antibody to highlight AML cells, instead of CD117 to avoid any unexpected effect from Apt-MTX treatment. Residual AML cells (%) in each specimen were quantified by flow cytometry based on cellular CD34 expression. In comparing to non-treatment control group, Apt-MTX treatment selectively inhibited AML cells and had no effect on growth of background marrow cells (FIG. 7A). The Apt-MTX treatment resulted in significant changes in ratios of AML cells vs. background marrow cells in each patient specimen (FIGS. 7B and 7C). These findings demonstrated that the CD117-specific Apt-MTX was able to selectively target and inhibit AML cells and more importantly, have no toxicity to normal marrow cells (FIG. 7D).

Figure 5:
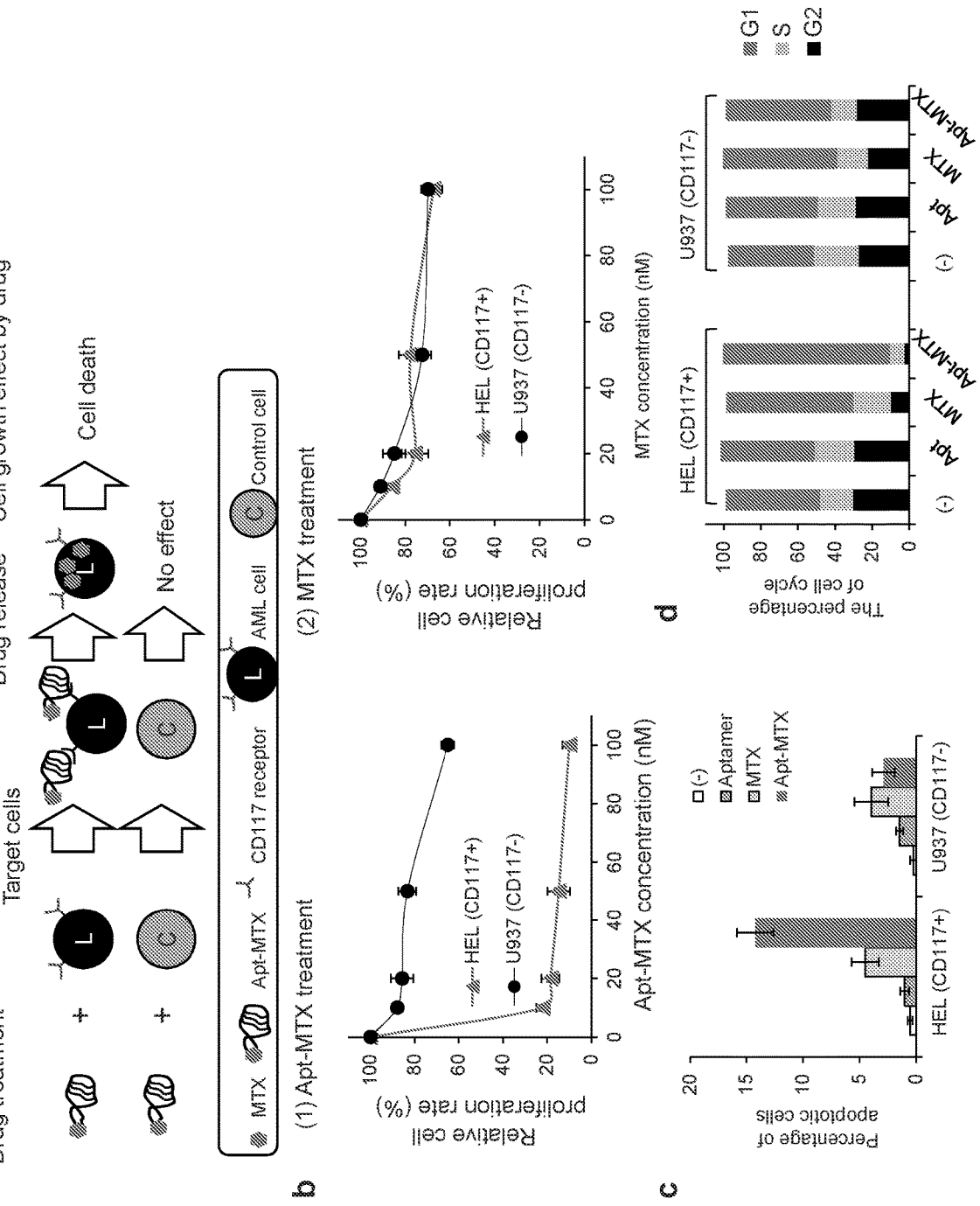
FIG. 5 shows Apt-MTX treatment specifically reducing cell growth of CD117-positive cells HEL, no effect on CD117-negative cells U937 (a) A schematic of Apt-MTX treatment and the specific effect of Apt-MTX on target and off-target cells. (b) CD117-positive cells HEL and CD117-negative cells U937 were treated by Apt-MTX, respectively for 2 hours. Equal molar amount of free MTX was used in control treatment experiments. Post culture for 48 hours, changes in proliferation rates (5) of the treated cells were detected by MTT assay. (c) Apt-MTX specifically induced apoptosis in CD117-positive cells HEL, but not in CD117-negative cells U937. Equal molar amounts of aptamer and free MTX were considered as control treatments. Both cells showed similar sensitivity to aptamer alone or free MTX treatment. (d) The treated cells by Apt-MTX, equal molar amounts of free MTX or aptamer alonewere stained by Propidium Iodide, then, analyzed by flow cytometry to determine the percentage (%) of cell cycle G1, S and G2.
Figure 6:
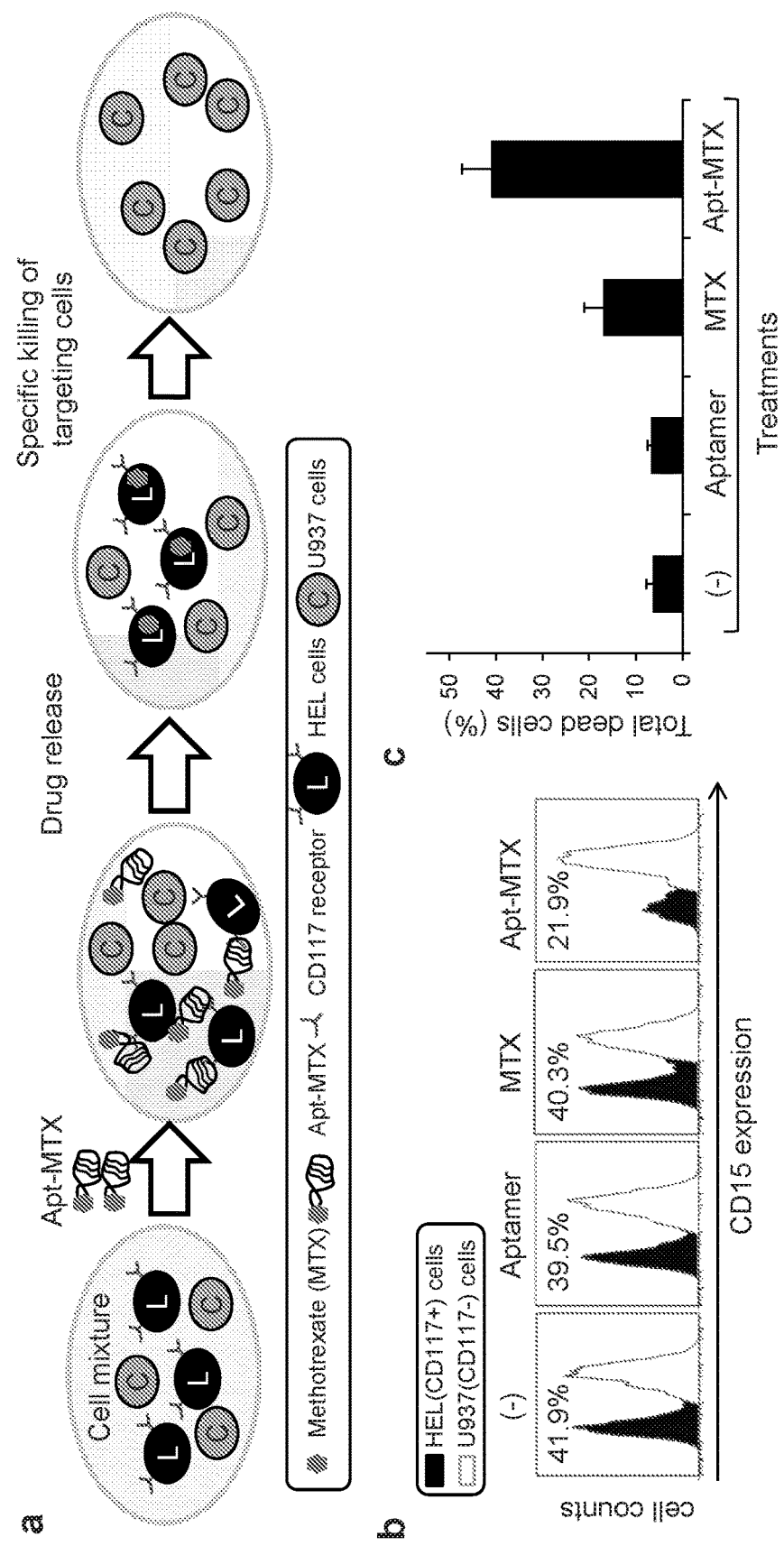
FIG. 6 shows specific killing of CD117-positive cells in simulated physiological conditions: (a) A schematic of cell mixture treatment by Apt-MTX. (b) Mixture of CD117-positive cells HEL and CD117-negative cell U937 were treated by Apt-MTX or equal molar MTX, respectively. As CD15 is expressed in U937, not in HEL, the treated cells in mixtures were distinguished by staining with anti-CD15 antibody. The ratio of the viable HEL and U937 cells in the same mixtures were then quantified by flow cytometry analysis. Compared with non-treated cells and aptamer alone or free MTX-treated cells, Apt-MTX treatment significantly decreased the ratio of HEL and U937 in the same mixtures. (c) Percentage of total dead cells was detected in the treated cell mixtures. Notably, Apt-MTX treatment induced more total cell death than equal molar free MTX treatment.

As a chemotherapy drug, Methotrexate (MTX) has been a vital component of successful all treatment regimens, regardless of immunophenotype of AML. The MTX treatment required high dose administration, which may cause methotrexate-induced nephrotoxicity, and can lead to acute renal failure (Ackland S P, Schilsky R L: High-dose methotrexate: a critical reappraisal. Journal of clinical oncology: official journal of the American Society of Clinical Oncology 1987, 5(12):2017-2031; Widemann B C, Adamson P C: Understanding and managing methotrexate nephrotoxicity. The oncologist 2006, 11(6):694-703; Buchen S, Ngampolo D, Melton R G, Hasan C, Zoubek A, Henze G, Bode U, Fleischhack G: Carboxypeptidase G2 rescue in patients with methotrexate intoxication and renal failure. British journal of cancer 2005, 92(3):480-487). To reduce MTX side effects on normal cells/tissues and retain its therapeutic effect, AML cell-targeted drug delivery approach is indispensable. To this end, a novel Apt-MTX was formulated by using a CD117-specific aptamer sequence, disclosed herein. Validation studies showed that through aptamer-guidance to AML cells, Apt-MTX with sub-toxic dose was able to deliver and selectively accumulate MTX to reach therapeutic threshold within targeted cells, leading to cultured AML cell death and no toxicity on off-target control cells (FIGS. 5 and 6). In addition, treatment studies of patient specimens revealed that the Apt-MTX selectively inhibited primary AML cells, and had no effect on growth of normal marrow cells within the same patient specimens (FIG. 7), indicating its potential for clinical targeted therapy usage. Although single Apt-MTX treatment with sub-toxic dose did not completely eliminate primary AML cells in patient specimens, its therapeutic efficacy could be improved by repeated treatments, and/or in combination with other drug treatment similar to chemotherapeutic regimen for AML clinically. Moreover, as chemical antibodies, oligonucleotide aptamers can be easily modified and conjugated with multiple therapeutic agents through physical and/or chemical reactions (Bruno J G: A review of therapeutic aptamer conjugates with emphasis on new approaches. Pharmaceuticals 2013, 6(3):340-357; Estevez M C, Huang Y F, Kang H, O'Donoghue M B, Bamrungsap S, Yan J, Chen X, Tan W: Nanoparticle-aptamer conjugates for cancer cell targeting and detection. Methods in molecular biology 2010, 624:235-248), resulting in a synergistic effect. This Apt-MTX demonstrates a new approach for targeted AML therapy, and more importantly, provides a universal platform for developing new targeted therapeutics to different cancers by simply replacing aptamer sequence specific for biomarker of interest.

What is claimed is:

1. An aptamer-agent conjugate comprising: a nucleic acid aptamer comprising a region that specifically binds with a CD117 cell, and an agent, wherein the nucleic acid aptamer comprises SEQ ID NO: 1 or SEQ ID NO: 4 or SEQ ID NO: 5 or SEQ ID NO: 6.

2. The conjugate of claim 1, wherein the agent is a small molecule, organometallic compound, nucleic acid, protein, peptide, lipid, carbohydrate, hormone, metal, radioactive element, gelonin, phototoxic agent, drug, vaccine, or immunological agent.

3. The conjugate of claim 1, wherein the agent can link with more than one aptamer.

4. The conjugate of claim 1, wherein the agent is a therapeutic agent.

5. The conjugate of claim 4, wherein the therapeutic agent causes apoptosis of CD117 cells.

6. The conjugate of claim 4, wherein the therapeutic agent is methotrexate.

7. An isolated nucleic acid molecule comprising SEQ ID NO: 1 or SEQ ID NO: 4 or SEQ ID NO: 5 or SEQ ID NO: 6.

8. An expression cassette comprising the nucleic acid molecule of claim 7.

9. A vector comprising the nucleic acid molecule of claim 7.

10. A pharmaceutical composition comprising the conjugate of claim 1, wherein the agent is a therapeutic agent.

11. The pharmaceutical composition of claim 10, wherein the composition further comprises at least two therapeutic agents.

12. The pharmaceutical composition of claim 10, wherein the therapeutic agents are selected from the group consisting of methotrexate, an antagonist of fibroblast-growth factor (FGF), hepatocyte growth factor (HGF) tissue factor (TF), protein C, protein S, platelet-derived growth factor (PDGF), heregulin, macrophage-stimulating protein (MSP) and vascular endothelial growth factor (VEGF), and an antagonist of a receptor for epidermal-growth factor (EGF), fibroblast-growth factor (FGF), hepatocyte growth factor (HGF, tissue factor (TF), protein C, protein S, platelet-derived growth factor (PDGF), heregulin, macrophage-stimulating protein (MSP) and vascular endothelial growth factor (VEGF) including FIER2 receptor, FIER3 receptor, c-MET, and other receptor tyrosine kinases.

13. A method of targeting CD117 cells with an agent, the method comprising conjugating a nucleic acid aptamer comprising a region that interacts with a CD117 cell to the agent, and exposing CD117 cells to the aptamer/agent conjugate, wherein the nucleic acid comprises SEQ ID NO: 1 or SEQ ID NO: 4 or SEQ ID NO: 5 or SEQ ID NO: 6.

14. The method of claim 13, wherein the agent is a mall molecule, organometallic compound, nucleic acid, protein, peptide, lipid, carbohydrate, hormone, metal, radioactive element, gelonin, phototoxic agent, drug, vaccine, or immunological agent.

15. The method of claim 13, wherein the agent is a therapeutic agent.

16. The method of claim 15, wherein the therapeutic agent causes apoptosis of CD117.

17. A method of treating a subject with acute myeloid leukemia, the method comprising: identifying a subject in need of treatment for acute myeloid leukemia, and administering a pharmaceutical composition to the subject, wherein the pharmaceutical composition comprises a conjugate of a nucleic acid aptamer and a cancer treating agent, wherein the nucleic acid aptamer comprises a region that interacts with a CD117 cell, thereby treating acute myeloid leukemia in the subject, wherein the nucleic acid aptamer comprises the nucleic acid aptamer of claim 1.

18. The method of claim 17, wherein the agent is a small molecule, organometallic compound, nucleic acid, protein, peptide, lipid, carbohydrate, hormone, metal, radioactive element, gelonin, phototoxic agent, drug, vaccine, or immunological agent.

19. The method of claim 17, wherein the cancer-treating agent is methotrexate.

* * * * *